United States Patent [19]

Center et al.

[11] Patent Number: 5,766,866

[45] Date of Patent: Jun. 16, 1998

[54] LYMPHOCYTE CHEMOATTRACTANT FACTOR AND USES THEREOF

[75] Inventors: David M. Center, Wellesley Hills; William W. Cruikshank, Westford; Hardy Kornfeld, Brighton, all of Mass.

[73] Assignee: Research Corporation Technologies, Inc., Tucson, Ariz.

[21] Appl. No.: 580,680

[22] Filed: Dec. 29, 1995

Related U.S. Application Data

[60] Division of Ser. No. 480,156, Jun. 7, 1995, which is a continuation-in-part of Ser. No. 354,961, Dec. 13, 1994, which is a continuation of Ser. No. 68,949, May 21, 1993, abandoned.

[51] Int. Cl.$^6$ ............... G01N 33/53; C07K 1/00; C07K 16/00; A61K 45/05
[52] U.S. Cl. ............... 424/7.24; 435/7.1; 435/7.92; 435/975; 530/350; 530/351; 530/387.1; 530/388.23; 530/389.2; 424/85.1; 424/130.1
[58] Field of Search ............... 435/7.24, 7.1, 435/7.92, 975; 530/350, 351, 387.1, 388.23, 389.2; 424/130.1, 85.1

[56] References Cited

U.S. PATENT DOCUMENTS 4,486,530  12/1984  David et al. .
4,745,051  5/1988  Smith et al. .

FOREIGN PATENT DOCUMENTS

WO 94/28134  12/1994  WIPO .

OTHER PUBLICATIONS

Berman, et al., Cellular Immunology, 95:105–112 (1985).
Berman, et al., AM Rev. Respir. Dis., 142:238–257 (1990).
Cambell, "Monoclonal Antibody Technology, The Production and Characterization of Rodent and Human Hybridomas," Elsevier Science Publishers (Amsterdam), pp. 1–4 and 29 (1984).

Center, et al., The Journal of Immunology, 128:2563–2568 (1982).

Cruikshank, et al., The Journal of Immunology, 138:3817–3823 (1987).

Cruikshank, et al., The Journal of Immunology, 146:2928–2934 (1991).

Cruikshank, et al., EMBL Database, Accession No. M90301 (1992).

Cruikshank, et al., The Journal of Immunology, 128:2569–2574 (1982).

Rand, et al., J. Exp. Med., 173:1521–1528 (1991).

Harlow (1988) Antibodies, a laboratory manual, Cold Spring Harbor Laboratory, 285, 287.

Waldman (1991) Science, vol. 252, 1657–1662.

Hams et al (1993) TIBTECH Feb. 1993 vol. 111, 42–44.

Center, et al. (Feb. 1995) "The Lymphocyte Chemoattractant Factor", J. Lab. Clin. Med. 125(2):167–172.

Cruikshank, et al. (May 24, 1994) "Molecular and Functional Analysis of a Lymphocyte Chemoattractant Factor: Association of Biologic Function with CD4 Expression", Proc. Natl. Acad. Sci. USA 91(11):5109–5113.

(May 1996) "Terminology Note: Interleukin 16 (IL–16)", Eur. J. Immunol. 26(5)1196.

Primary Examiner—Anthony C. Caputa
Assistant Examiner—Khalid Masood
Attorney, Agent, or Firm—Scully, Scott, Murphy & Presser

[57] ABSTRACT

Disclosed is a substantially pure antibody which specifically binds a LCF polypeptide and methods of using such antibodies.

5 Claims, 19 Drawing Sheets

| | |
|---|---|
| 1 | TTCCTCGAGAGCTGTCAACACAGGCTGAGGAATCTCAAGGCCCAGTGCTCAAGATGCCT |
| 60 | AGCCAGCGAGCACGGAGCTTCCCCCTGACCAGGTCCCAGTCCTGTGAGACGAAGCTACT |
| 119 | TGACGAAAAGACCAGCAAACTCTATTCTATCACCAGCCAGTGTCATCGGCTGTCATGAA |
| 178 | ATCCTTGCTGTGCCTTCCATCTTCTATCTCCTGTGCCCAGACTCCCTGCATCCCCAAGG |
| 237 | CAGGGGCATCTCCAACATCATCATCCAACGAAGACTCAGCTGCAAATGGTTCTGCTGAA |
| 296 | ACATCTGCCTTGGACACGGGGTTCTCGCTCAACCTTTCAGAGCTGAGAGAATATACAGA |
| 355 | GGGTCTCACGGAAGCCAAGGAAGACGATGATGGGGACCACAGTTCCTTCAGTCTGGTCA |
| 414 | GTCCGTTATCTCCCTGCTGAGCTCAGAAGAATTAAAAAAACTCATCGAGGAGGTGAAGG |
| 473 | TTCTGGATGAAGCAACATTAAAGCAATTAGACGGCATCCATGTCACCATCTTACACAAG |
| 532 | GAGGAAGGTCGTGGTCTTGGGTTCAGCTTGGCAGGAGGAGCAGATCTAGAAAACAAGGT |
| 591 | GATTACGGTTCACAGAGTGTTTCCAAATGGGCTGGCCTCCCAGGAAGGGACTATTCAGA |
| 650 | AGGGCAATGAGGTTCTTTCCATCAACGGCAAGTCTCTCAAGGGGACCACGCACCATGAT |
| 709 | GCCTTGGCCATCCTCCGCCAAGCTCGAGAGCCCAGGCAAGCTGTGATTGTCACAAGGAA |
| 768 | GCTGACTCCAGAGCC ATG CCC GAC CTC AAC TCC TCC ACT GAC TCT GCA |
| 1 |                Met Pro Asp Leu Asn Ser Ser Thr Asp Ser Ala |
| 816 | GCC TCA GCC TCT GCA GCC AGT GAT GTT TCT GTA GAA TCT ACA GCA |
| 12 | Ala Ser Ala Ser Ala Ala Ser Asp Val Ser Val Glu Ser Thr Ala |
| 861 | GAG GCC ACA GTC TGC ACG GTG ACA CTG GAG AAG ATG TCG GCA GGG |
| 27 | Glu Ala Thr Val Cys Thr Val Thr Leu Glu Lys Met Ser Ala Gly |
| 906 | CTG GGC TTC AGC CTG GAA GGA GGG AAG GGC TCC CTA CAC GGA GAC |
| 42 | Leu Gly Phe Ser Leu Glu Gly Gly Lys Gly Ser Leu His Gly Asp |
| 951 | AAG CCT CTC ACC ATT AAC AGG ATT TTC AAA GGA GCA GCC TCA GAA |
| 57 | Lys Pro Leu Thr Ile Asn Arg Ile Phe Lys Gly Ala Ala Ser Glu |
| 996 | CAA AGT GAG ACA GTC CAG CCT GGA GAT GAA ATC TTG CAG CTG GGT |
| 72 | Gln Ser Glu Thr Val Gln Pro Gly Asp Glu Ile Leu Gln Leu Gly |
| 1041 | GGC ACT GCC ATG CAG GGC CTC ACA CGG TTG GAA GCC TGG AAC ATC |
| 87 | Gly Thr Ala Met Gln Gly Leu Thr Arg Phe Glu Ala Trp Asn Ile |
| 1086 | ATC AAG GCA CTG CCT GAT GGA CCT GTC ACG ATT GTC ATC AGG AGA |
| 102 | Ile Lys Ala Leu Pro Asp Gly Pro Val Thr Ile Val Ile Arg Arg |
| 1131 | AAA AGC CTC CAG TCC AAG GAA ACC ACA GCT GCT GGA GAC TCC TAG |
| 117 | Lys Ser Leu Gln Ser Lys Glu Thr Thr Ala Ala Gly Asp Ser  - |
| 1176 | GCAGGACATGCTGAAGCCAAAGCCAATAACACACAGCTAACACACAGCTCCCATAACCG |
| 1235 | CTGATTCTCAGGGTCTCTGCTGCCGCCCCACCCAGATGGGGGAAAGCACAGGTGGGCTT |
| 1294 | CCCAGTGGCTGCTGCCCAGGCCCAGACCTTCTAGGACGCCACCCAGCAAAAGGTTGTTC |
| 1353 | CTAAAATAAGGGCAGAGTCACACTGGGGCAGCTGATACAAATTGCAGACTGTGTAAAAA |
| 1412 | GAGAGCTTAATGATAATATTGTGGTGCCACAAATAAAATGGATTTATTAGAATTCCATA |
| 1471 | TGACATTCATGCCTGGCTTCGCAAAATGTTTCAAGTACTGTAACTGTGTCATGATTCAC |
| 1530 | CCCCAAACAGTGACATTTATTTTTCTCATGAATCTGCAATGTGGGCAGAGATTGGAATG |
| 1589 | GGCAGCTCATCTCTGTCCCACTTGGCATCAGCTGGCGTCATGCAAAGTCATGCAAAGGC |
| 1648 | TGGGACCACCTGAGATCATTCACTCATACATCTGGCCGTTGATGTTGGCTGGGAACTCA |
| 1707 | CCTGGGGCTGCTGGCCTGAATGCTTATAGGTGGCCTCTCCTTGTTGCCTGGGCTCCTCA |
| 1755 | CAACATGGTGTCTGGATTCCCAGGATGAGCATCCCAGGATCGCAAGAGCCACGTAGAAG |
| 1825 | CTGCATCTTGTTTATACCTTTGCCTTGGAAGTTGCATGGCATCACCTCCACCATACTCC |
| 1884 | ATCAGTTAGAGCTGACACAAACCTGCCTGGGTTTAAGGGGAGAGGAAATATTGCTGGGG |
| 1943 | TCATTTATGAAAAATACAGTTTGTCACATGAAACATTTGCAAAATTGTTTTTGGTTGGA |
| 2002 | TTGGAGAAGTAATCCTAGGGAAGGGTGGTGGAGCCAGTAAATAGAGGAGTACAGTGTAA |
| 2061 | GCACCAAGCTCAAAGCGTGGACAGGTGTGCCGACAGAAGGAACCAGCGTGTATATGAGG |
| 2120 | GTATCAAATAAAATTGCTACTACTTACCACC |

FIG.2

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 130 amino acids
      ( B ) TYPE: amino acid
      ( C ) STRANDEDNESS: Not Relevant
      ( D ) TOPOLOGY: linear ( i i ) MOLECULE TYPE: protein ( x i ) SEQUENCE DESCRIPTION: SEQ ID NO:1:

```
Met Pro Asp Leu Asn Ser Ser Thr Asp Ser Ala Ala Ser Ala Ser Ala
 1               5                  10                  15
Ala Ser Asp Val Ser Val Glu Ser Thr Ala Glu Ala Thr Val Cys Thr
                20                  25                  30
Val Thr Leu Glu Lys Met Ser Ala Gly Leu Gly Phe Ser Leu Glu Gly
            35                  40                  45
Gly Lys Gly Ser Leu His Gly Asp Lys Pro Leu Thr Ile Asn Arg Ile
        50                  55                  60
Phe Lys Gly Ala Ala Ser Glu Gln Ser Glu Thr Val Gln Pro Gly Asp
 65                 70                  75                  80
Glu Ile Leu Gln Leu Gly Gly Thr Ala Met Gln Gly Leu Thr Arg Phe
                85                  90                  95
Glu Ala Trp Asn Ile Ile Lys Ala Leu Pro Asp Gly Pro Val Thr Ile
            100                 105                 110
Val Ile Arg Arg Lys Ser Leu Gln Ser Lys Glu Thr Thr Ala Ala Gly
        115                 120                 125
Asp Ser
130
```

( 2 ) INFORMATION FOR SEQ ID NO:2:

( i ) SEQUENCE CHARACTERISTICS:
      ( A ) LENGTH: 2150 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:2:

```
TTCCTCGAGA  GCTGTCAACA  CAGGCTGAGG  AATCTCAAGG  CCCAGTGCTC  AAGATGCCTA      60
GCCAGCGAGC  ACGGAGCTTC  CCCCTGACCA  GGTCCAGTC   CTGTGAGACG  AAGCTACTTG     120
ACGAAAAGAC  CAGCAAACTC  TATTCTATCA  CCAGCCAGTG  TCATCGGCTG  TCATGAAATC     180
CTTGCTGTGC  CTTCCATCTT  CTATCTCCTG  TGCCCAGACT  CCCTGCATCC  CCAAGGCAGG     240
GGCATCTCCA  ACATCATCAT  CCAACGAAGA  CTCAGCTGCA  AATGGTTCTG  CTGAAACATC     300
TGCCTTGGAC  ACGGGGTTCT  CGCTCAACCT  TTCAGAGCTG  AGAGAATATA  CAGAGGGTCT     360
CACGGAAGCC  AAGGAAGACG  ATGATGGGGA  CCACAGTTCC  TTCAGTCTGG  TCAGTCCGTT     420
ATCTCCCTGC  TGAGCTCAGA  AGAATTAAAA  AAACTCATCG  AGGAGGTGAA  GGTTCTGGAT     480
```

| | | | | | | |
|---|---|---|---|---|---|---|
| GAAGCAACAT | TAAAGCAATT | AGACGGCATC | CATGTCACCA | TCTTACACAA | GGAGGAAGGT | 540 |
| CGTGGTCTTG | GGTTCAGCTT | GGCAGGAGGA | GCAGATCTAG | AAAACAAGGT | GATTACGGTT | 600 |
| CACAGAGTGT | TTCCAAATGG | GCTGGCCTCC | CAGGAAGGGA | CTATTCAGAA | GGGCAATGAG | 660 |
| GTTCTTTCCA | TCAACGGCAA | GTCTCTCAAG | GGGACCACGC | ACCATGATGC | CTTGGCCATC | 720 |
| CTCCGCCAAG | CTCGAGAGCC | CAGGCAAGCT | GTGATTGTCA | CAAGGAAGCT | GACTCCAGAG | 780 |
| CCATGCCCGA | CCTCAACTCC | TCCACTGACT | CTGCAGCCTC | AGCCTCTGCA | GCCAGTGATG | 840 |
| TTTCTGTAGA | ATCTACAGCA | GAGGCCACAG | TCTGCACGGT | GACACTGGAG | AAGATGTCGG | 900 |
| CAGGGCTGGG | CTTCAGCCTG | GAAGGAGGGA | AGGGCTCCCT | ACACGGAGAC | AAGCCTCTCA | 960 |
| CCATTAACAG | GATTTTCAAA | GGAGCAGCCT | CAGAACAAAG | TGAGACAGTC | CAGCCTGGAG | 1020 |
| ATGAAATCTT | GCAGCTGGGT | GGCACTGCCA | TGCAGGGCCT | CACACGGTTG | GAAGCCTGGA | 1080 |
| ACATCATCAA | GGCACTGCCT | GATGGACCTG | TCACGATTGT | CATCAGGAGA | AAAAGCCTCC | 1140 |
| AGTCCAAGGA | AACCACAGCT | GCTGGAGACT | CCTAGGCAGG | ACATGCTGAA | GCCAAAGCCA | 1200 |
| ATAACACACA | GCTAACACAC | AGCTCCCATA | ACCGCTGATT | CTCAGGGTCT | CTGCTGCCGC | 1260 |
| CCCACCCAGA | TGGGGGAAAG | CACAGGTGGG | CTTCCCAGTG | GCTGCTGCCC | AGGCCCAGAC | 1320 |
| CTTCTAGGAC | GCCACCCAGC | AAAAGGTTGT | TCCTAAAATA | AGGGCAGAGT | CACACTGGGG | 1380 |
| CAGCTGATAC | AAATTGCAGA | CTGTGTAAAA | AGAGAGCTTA | ATGATAATAT | TGTGGTGCCA | 1440 |
| CAAATAAAAT | GGATTTATTA | GAATTCCATA | TGACATTCAT | GCCTGGCTTC | GCAAAATGTT | 1500 |
| TCAAGTACTG | TAACTGTGTC | ATGATTCACC | CCCAAACAGT | GACATTTATT | TTTCTCATGA | 1560 |
| ATCTGCAATG | TGGGCAGAGA | TTGGAATGGG | CAGCTCATCT | CTGTCCCACT | TGGCATCAGC | 1620 |
| TGGCGTCATG | CAAAGTCATG | CAAAGGCTGG | GACCACCTGA | GATCATTCAC | TCATACATCT | 1680 |
| GGCCGTTGAT | GTTGGCTGGG | AACTCACCTG | GGGCTGCTGG | CCTGAATGCT | TATAGGTGGC | 1740 |
| CTCTCCTTGT | TGCCTGGGCT | CCTCACAACA | TGGTGTCTGG | ATTCCAGGA | TGAGCATCCC | 1800 |
| AGGATCGCAA | GAGCCACGTA | GAAGCTGCAT | CTTGTTTATA | CCTTTGCCTT | GGAAGTTGCA | 1860 |
| TGGCATCACC | TCCACCATAC | TCCATCAGTT | AGAGCTGACA | CAAACCTGCC | TGGGTTTAAG | 1920 |
| GGGAGAGGAA | ATATTGCTGG | GGTCATTTAT | GAAAAATACA | GTTTGTCACA | TGAAACATTT | 1980 |
| GCAAAATTGT | TTTTGGTTGG | ATTGGAGAAG | TAATCCTAGG | GAAGGGTGGT | GGAGCCAGTA | 2040 |
| AATAGAGGAG | TACAGTGTAA | GCACCAAGCT | CAAAGCGTGG | ACAGGTGTGC | CGACAGAAGG | 2100 |
| AACCAGCGTG | TATATGAGGG | TATCAAATAA | AATTGCTACT | ACTTACCACC | | 2150 |

LYMPHOCYTE CHEMOATTRACTANT FACTOR AND USES THEREOF

This is a divisional of application Ser. No. 08/480,156, filed on Jun. 7, 1995; which is a continuation-in-part of U.S. Ser. No. 08/354,961, filed Dec. 13, 1994; which is a continuation of U.S. Ser. No. 08/068,949, filed May 21, 1993 now abandoned.

This work was supported in part by a grant from the Federal Government and the Government therefore has certain rights in the invention.

BACKGROUND OF THE INVENTION

This invention relates to recombinant LCF, DNA, and uses thereof.

CD4, a cell-cell adhesion protein, is expressed on a subset of T lymphocytes (Krensky et al., *Proc. Natl. Acad. Sci. U.S.A.* 79:2365–2369, 1982; Biddison et al., *J. Exp. Med.* 156:1065–1076, 1982; and Wilde et al., *J. Immunol.* 131:152–157, 1983), mononuclear cells (Stewart et al., *J. Immunol.* 136:3773–3778, 1986), and eosinophils (Rand et al., *J. Exp. Med.* 173:1521–1528, 1991). In lymphocytes, CD4 contributes to antigen receptor signaling (Collins et al., *J. Immunol.* 148:2159–2162, 1992; Anderson et al., *J. Immunol.* 139–678–682, 1987; Eichmann et al., *J. Immunol.* 17:643–650, 1987; Walker et al., *Eur. J. Immunol.* 17:873–880 1987; and Sleckman et al., *Nature* 328:351–353, 1987) by direct interaction with MHC Class II molecules (Doyle et al., *Nature* 330:256–259, 1987). In addition, a natural soluble lymphokine, lymphocyte chemoattractant factor (LCF), requires cell surface expression of CD4 to induce chemotactic activity in monocytes (Cruikshank et al., *J. Exp. Med.* 173:1521–1528, 1991) and T lymphocytes (Cruikshank et al., *J. Immunol.* 138:3817–3823, 1987; Cruikshank et al., *J. Immunol.* 146:2928–2934, 1991). In concert with its chemoattractant activity LCF acts as a competence growth factor for human T lymphocytes (Cruikshank et al., *J. Immunol.* 138:3817–3823, 1987).

LCF is a cationic, 56-kD glycoprotein representing the tetrameric form of four 14-kD monomeric chains. LCF is produced by T lymphocytes and is specifically chemoattractant for CD4+ T-cells, monocytes and eosinophils (see, e.g., Berman et al. *Cell Immunol.* 95:105–112, 1985; Rand et al., *JEM* 173:1521–1528, 1991). Secretion of LCF by CD8+ T cells occurs (Cruikshank et al., *J. Immunol.* 138:3817, 1987;) after stimulation by mitogen, antigen, histamine or serotonin. The latter two are of particular interest because degranulated mast cells and basophils are present in tissue sites of delayed-type hypersensitivity reactions (see, e.g., Askenase Prog. *Allergy* 23:199–320, 1977). Induction of LCF by a mast cell or a basophil product provides a link between the early mediator phase of the immune response and the development of the later T-lymphocyte-predominant inflammatory reaction.

SUMMARY OF THE INVENTION

In general, the invention features recombinant lymphocyte chemoattractant factor (LCF) polypeptide, e.g., LCF produced in a prokaryotic or baculovirus expression system. Preferably, the polypeptide includes an amino acid sequence substantially identical to the amino acid sequence shown in FIG. 2 (SEQ ID NO: 1). By "lymphocyte chemoattractant factor polypeptide" is meant all or part of a protein which specifically binds CD4 and signals the appropriate LCF-mediated cascade of biological events, e.g., a polypeptide capable of promoting or stimulating the migration of unactivated or activated CD4+lymphocytes, eosinophils, monocytes, and the like. By "polypeptide" is meant any chain of amino acids, regardless of length or post-translational modification (e.g., glycosylation). By a "substantially identical" amino acid sequence is meant an amino acid sequence which differs only by conservative amino acid substitutions, for example, substitution of one amino acid for another of the same class (e.g., valine for glycine, arginine for lysine and the like) or by one or more non-conservative amino acid substitutions, deletions, or insertions located at positions of the amino acid sequence which do not destroy the biological activity of the polypeptide. Such equivalent polypeptides can be isolated by extraction from tissues or cells of any animal which naturally produce such a polypeptide or which can be induced to do so, using the methods described below, or their equivalent; or can be isolated by chemical synthesis; or can be isolated by standard techniques of recombinant DNA technology, e.g., by isolation of cDNA or genomic DNA encoding such a polypeptide.

In another aspect, the invention features a fragment or analog of LCF which exhibits LCF agonist or antagonist activity. The invention thus includes any biologically active fragment or analog of LCF polypeptide. By "biologically active" is meant possessing any activity which is characteristic of the 130-amino acid LCF polypeptide shown in FIG. 2 (SEQ ID NO: 1). Because LCF polypeptide exhibits a range of physiological properties and because such properties may be attributable to different portions of the LCF polypeptide molecule, a useful LCF polypeptide fragment or LCF polypeptide analog is one which exhibits a biological activity in any biological assay for LCF polypeptide activity, for example, those assays described herein. Most preferably it possesses 10%, preferably 40%, or at least 90% of the activity of LCF polypeptide (shown in FIG. 2; SEQ ID NO: 1), in any LCF polypeptide assay.

Preferred analogs include LCF polypeptide (or biologically active fragments thereof) whose sequences differ from the wild-type sequence only by conservative amino acid substitutions, for example, substitution of one amino acid for another with similar characteristics (e.g., valine for glycine, arginine for lysine, and the like) or by one or more non-conservative amino acid substitutions, deletions, or insertions which do not abolish the polypeptide's biological activity. Other useful modifications include those which increase peptide stability; such analogs may contain, for example, one or more non-peptide bonds (which replace the peptide bonds) or D-amino acids in the peptide sequence.

Analogs can differ from naturally occurring LCF polypeptide in amino acid sequence or can be modified in ways that do not involve sequence, or both. Analogs of the invention will generally exhibit at least 70%, more preferably 80%, more preferably 90%, and most preferably 95% or even 99%, homology with a segment of 20 amino acid residues, preferably more than 40 amino acid residues, or more preferably the entire sequence of a naturally occurring LCF polypeptide sequence.

Alterations in primary sequence include genetic variants, both natural and induced. Also included are analogs that include residues other than naturally occurring L-amino acids, e.g., D-amino acids or non-naturally occurring or synthetic amino acids, e.g., β or γ amino acids. Alternatively, increased stability may be conferred by cyclizing the peptide molecule. Modifications include in vivo or in vitro chemical derivatization of polypeptides, e.g., acetylation, methylation, phosphorylation, phremylation, isupremylation, myristilation, carboxylation, or glycosylation; glycosylation can be modified. e.g.. by modifying the glycosylation patterns of a polypeptide during its synthesis and processing or in further processing steps. e.g.. by exposing the polypeptide to glycosylation affecting enzymes derived from cells that normally provide such processing. e.g.. mammalian glycosylation enzymes; phosphorylation can be modified by exposing the polypeptide to phosphorylation-altering enzymes. e.g.. kinases or phosphatases, etc. By "substantially pure" is meant that the LCF polypeptide provided by the invention is at least 60%. by weight. free from the proteins and naturally-occurring organic molecules with which it is naturally associated. Preferably. the preparation is at least 75%, more preferably at least 90%. and most preferably at least 99%, by weight. LCF polypeptide. A substantially pure LCF polypeptide may be obtained. for example. by extraction from a natural-source (e.g.. a human peripheral blood mononuclear cell) using the methods outlined below; or can be isolated by expression of a recombinant nucleic acid encoding a LCF polypeptide using the standard techniques of recombinant DNA technology. e.g.. by isolation of cDNA or genomic DNA encoding such an LCF polypeptide, or by chemically synthesizing the protein. fragment or analog thereof. Purity can be measured by any appropriate method. e.g.. column chromatography. polyacrylamide gel electrophoresis. or high-performance liquid chromatography (HPLC) analysis.

In another aspect. the invention features substantially pure DNA encoding a LCF polypeptide (or polypeptide fragment or analog thereof) as described above. Preferably. the DNA comprises a nucleotide sequence substantially identical to the nucleotide sequence shown in FIG. 2 (SEQ ID NO: 2). Moreover. such a DNA is cDNA and encodes a mammalian LCF polypeptide. e.g.. a human. The invention also features a vector which includes such substantially pure DNA and which is capable of directing expression of the protein encoded by the DNA in a vector-containing cell. The invention features a cell which contains the substantially pure DNA. The cell may be either prokaryotic. e.g.. *E. coli* or eukaryotic. e.g.. a mammalian cell or the cell of an arthropod. e.g.. a grasshopper.

By "substantially pure DNA" is meant DNA that is free of the genes which. in the naturally-occurring genome of the organism from which the DNA of the invention is derived. flank the gene. The term therefore includes. for example. a recombinant DNA which is incorporated into a vector; into an autonomously replicating plasmid or virus; or into the genomic DNA of a prokaryote or eukaryote; or which exists as a separate molecule (e.g.. a cDNA or a genomic or cDNA fragment produced by polymerase chain reaction-(PCR) methodologies or restriction endonuclease digestion) independent of other sequences. It also includes a recombinant DNA which is part of a hybrid gene encoding additional polypeptide sequence.

In another aspect. the invention features a method of producing a recombinant LCF polypeptide (or a fragment or analog thereof). The method involves (a) providing a cell (e.g., *E. coli* or *S. frugidera* transformed with DNA encoding a LCF polypeptide or a fragment or analog thereof positioned for expression in the cell; (b) culturing the transformed cell under conditions for expressing the DNA; and (c) isolating the recombinant LCF polypeptide. By "transformed cell" is meant a cell into which (or into an ancestor of which) has been introduced. by means of recombinant techniques. a DNA molecule encoding (as used herein) an LCF polypeptide. Such a DNA molecule is "positioned for expression" meaning that the DNA molecule is positioned adjacent to a DNA sequence which directs transcription and translation of the sequence (i.e.. facilitates the production of. e.g. LCF. or fragment or analog thereof).

In still another aspect. the invention features a substantially pure antibody which binds preferentially to a LCF (or a fragment or analog thereof). By "substantially pure antibody" is meant antibody which is at least 60%. by weight. free from the proteins and naturally-occurring organic molecules with which it is naturally associated. Preferably. the preparation is at least 75%, more preferably at least 90%, and more preferably at least 99%. by weight. antibody. e.g.. LCF antibody. A substantially pure LCF antibody may be obtained. for example. by affinity chromatography using recombinantly-produced LCF polypeptide and standard techniques. Furthermore. the purified antibody is sufficiently free of other proteins. carbohydrates. and lipids with which it is naturally associated to permit therapeutic administration. Such an antibody "preferentially binds" to an LCF polypeptide (or a fragment or analog thereof). i.e.. does not substantially recognize and bind to other antigenically-unrelated molecules.

Preferably. the antibody neutralizes the biological activity of the protein to which it binds. By "neutralize" is meant to partially or completely block (e.g.. the biological activity of a LCF polypeptide).

In other aspects. the polypeptides or antibodies described above are used as the active ingredient of therapeutic compositions. In such therapeutic compositions. the active ingredient is formulated with a physiologically-acceptable carrier. These therapeutic compositions are used in a method of suppressing or mimicking LCF-CD4 interaction mediated physiological response. In particular. these methods are used to reduce an immune response. or inflammation. or growth of an unwanted cell. Compounds useful in practicing the method include. without limitation. an LCF antibody. or an LCF fragment or analog. or a drug. e.g. an organic compound.

In another aspect. the invention features an LCF immunoassay kit including an antibody of the invention. Preferably. such a kit includes a means for detecting the binding of the antibody to the LCF polypeptide.

In another aspect. the invention features a method of detecting LCF in a biological sample. the method involving (a) contacting the biological sample with an antibody of the invention; and (b) detecting immune complex formation between the antibody and a sample constituent as indicative of the presence of LCF in the sample. Preferably. the method involves an immune complex formation which is detected by an ELISA or a Western blot analysis.

In yet another aspect. the invention features a method of screening candidate compounds for their ability to inhibit interaction between LCF and CD4. The method involves: a) mixing a candidate antagonist compound with LCF; b) measuring LCF-CD4 binding; and c) identifying antagonistic compounds as those that interfere with the binding.

In still another aspect. the invention features a method of screening candidate compounds for the ability to mimick LCF activity. the method involving: a) mixing a candidate agonist compound with CD4 receptor; b) measuring binding of the compound to CD4 receptor; and c) identifying agonist compounds as those that bind CD4 receptor and mediate cell migration.

In another aspect. the invention features a composition for stimulating proliferation of CD4+ T-cells in a mammal. the composition including LCF and a growth factor. In preferred embodiments. the composition includes LCF and a growth factor in a ratio which causes synergy. e.g.. ranging from 1:100 to 1:1 (LCF to growth factor). Preferably, the growth factor is a cytokine e.g., IL-2, IL-4, IL-6, IL-7, IL-8, insulin, and insulin-like growth factor I.

The invention also features a method for stimulating proliferation of CD4+ T cells in a mammal, the method includes contacting cells with LCF and IL-2 together or close enough in time to cause synergy. In preferred embodiments, the method includes administering to a mammal (e.g., a human patient) an effective amount of LCF and a growth factor, wherein the proliferative activity of LCF in combination with the growth factor is greater than the proliferative activity of the LCF in the absence of the growth factor and the proliferative activity of the growth factor in the absence of LCF. In preferred embodiments the growth factor is a cytokine and, if desired, the administration of the composition occurs more than once.

In other preferred embodiments, the method for stimulating proliferation of CD4+ T cells involves (a) contacting cells with LCF and IL-2 in vitro and returning the proliferated cells into the mammal. Preferably, the stimulated CD4+ T cell is a PBMC or a HIV+PBMC. In other preferred embodiments, the method further involves contacting the cells with an anti-retroviral agent (e.g., AZT or ddI).

In another aspect, the invention features a method for stimulating proliferation of CD4+ T cells in a human infected with HIV, involving administering an effective therapeutic amount of a composition including LCF and a growth factor. In preferred embodiments, the infected human is an asymptomatic human infected with HIV. In still other preferred embodiments, the human infected with HIV has a CD4+ count greater than 50.

In another aspect, the invention features a method for stimulating proliferation of CD4+ in a human having an immune disorder, the method involving administering an effective therapeutic amount of a composition including LCF and a growth factor.

In another aspect, the invention features a method for inducing the proliferation of CD4+ T cells in a human, the method involving administering an effective therapeutic amount of a composition including LCF.

In still another aspect, the invention features a method of inhibiting a CD4+ bearing malignant cell in a mammal, involving administering to the mammal (e.g., a human patient), a therapeutically effective amount of an LCF antagonist (as described herein). In preferred embodiments, the CD4+ T cell is a lymphoma or is a leukemia. Preferably, the antagonist or inhibitor is a LCF fragment or analog thereof or is an anti-LCF antibody. In other preferred embodiments, the method further involves administering to the mammal a chemotherapeutic agent in an effective dose which is lower than the standard dose when the chemotherapeutic agent is used alone.

In another aspect, the invention features a method of protecting a mammal from developing a neoplasm, involving administering to the mammal (e.g., a human patient) a therapeutically effective amount of an LCF antagonist.

The proteins of the invention are involved in events leading to inducing the migration of specialized immune cells, e.g., eosinophils, monocytes, and T lymphocytes, which are important constituents and mediators of both the immune response and inflammation. Such proteins are therefore useful to treat or, alternatively, to develop therapeutics to treat hyperresponsive immune reactions and inflammation that pertain to the activation and subsequent infiltration of T lymphocytes, monocytes and eosinophils. Particular disorders which may be treated using the proteins and/or the methods of the present invention include, without limitation, any granulomatous immune reaction, e.g., as effected by tissue-invasive helminth parasites, cutaneous and respiratory late-phase reactions to allergens, asthma, sarcoidosis, hypersensitivity pneumonitis, interstitial pulmonary fibrosis, tuberculosis, rheumatoid arthritis, and lupus erythematous, allogenic organ transplant rejection, contact (cell-mediated) dermatitis,and immunologically mediated skin diseases (e.g. pemphigoid and bullous pemphigoid). A comprehensive text on the aforementioned disorders may be found in Principles of Internal Medicine 12th ed. (Wilson et al., McGraw Hill, Inc., New York). Preferred therapeutics include antagonists, e.g., peptide fragments, or antibodies, or drugs, which block LCF or LCF:CD4 receptor function by interfering with the LCF:CD4 receptor interaction and any concomitant biological activity directed by LCF. Similarly, the antibodies of the invention are useful for detecting the presence and clinical course of any disease associated with LCF, e.g., those disseases described above.

Recombinant LCF can also be used as an immunosuppressive agent or as part of immunosuppressive therapy. In particular, recombinant LCF may serve to attenuate, interrupt, or prevent the cascade of events that eventually result in immunological rejection of tissue or organ transplants. For example, recombinant LCF may be used to attenuate, interrupt, or prevent a patient from rejecting a kidney, lung, or combined heart-lung, or liver transplants. Further, recombinant LCF by virtue of its ability to interact and bind with CD4 receptors may be useful in the design of immunotoxins that selectively destroy CD4+ receptor bearing cells. Finally, recombinant LCF may be used, alone or in combination with other compounds (e.g. growth factors), to activate and replenish a CD4 lymphocyte population in any patient with a depleted population.

Because LCF may now be produced by recombinant techniques, and because candidate antagonists or agonists may be screened according to the assays described herein, the instant invention provides a simple and rapid approach to the identification of useful therapeutics. Such an approach was previously difficult because LCF was unavailable in sufficient quantities to identify its role in disease in animal models, and antibodies and DNA and RNA probes were previously unavailable for detection of LCF protein or gene expression in diseased tissues.

Thus, once identified, a peptide- or antibody-based therapeutic may be produced, in large quantity and inexpensively, using recombinant and molecular biological techniques, and the methods of the present invention. Finally, any chemical compound, e.g., an organic compound, may be easily screened according to the methods outlined herein in order to evaluate their effect on LCF:CD4 interaction.

Other features and advantages of the invention will be apparent from the following description of the preferred embodiments thereof, and from the claims.

DETAILED DESCRIPTION OF THE PREFERRED EMBODIMENTS DRAWINGS

The drawings will first be described.

FIG. 1 shows a northern analysis of LCF from total cellular RNA prepared from human T lymphocytes. Positions of 18S and 28S RNA visualized by ethidium bromide staining are shown at their respective arrows.

FIG. 2 shows the nucleotide sequence of the LCF-A cDNA (SEQ ID NO: 2) and predicted amino acid sequence of the encoded protein (SEQ ID NO: 1). Nucleotides are numbered on the left side beginning with the first nucleotide of the cDNA. The poly A tail begins immediately after the last indicated nucleotide (2152) and is omitted. Translation of the putative LCF coding sequence is indicated below the corresponding nucleotide sequence starting with Met. Each amino acid is consecutively numbered. An Asn residue (amino acid residue 5) represents a potential glycosylation site (marked with a dot). Two candidate polyadenylation signal sequences are underlined.

FIG. 3A and FIG. 3B show a SDS-PAGE of recombinant LCF expressed in E. coli and a rabbit reticulocyte in vitro translation of RNA synthesized from LCF cDNA . FIG. 3A shows recombinant LCF protein run on a 15% SDS-PAGE followed by coomassie blue staining. In FIG. 3A, lane A shows crude supernatant from E. coli induced to express LCF protein. lane B shows LCF protein generated as a fusion protein conjugated to a polyhistidine linker purified by nickel affinity chromatography, and lane C shows LCF after Factor Xa cleavage. The band at 17.5 kDa was blotted, excised and subjected to N-terminal amino acid sequencing. FIG. 3B shows a rabbit reticulocyte in vitro translation of LCF cDNA: the $^{35}$S-labeled protein product of LCF cDNA translated by rabbit reticulocytes was run on a 15% SDS-PAGE. In FIG. 3B, lane A shows LCF protein translated under non-glycosylating conditions, and lane B shows LCF translated under glycosylating conditions.

FIG. 4 shows the immunoprecipitation of recombinant LCF by rsCD4. In FIG. 4, lane 1 shows 10 µg of recombinant LCF; lane 2 shows recombinant LCF incubated with 50 µg rsCD4 immunoprecipitated with 10 µg rabbit polyclonal anti-CD4 antibody; lane 3 shows recombinant LCF incubated with 10 µg rsCD4 immunoprecipitated with polyclonal anti-CD4 antibody; lane 4 shows recombinant LCF incubated with rsCD4 (10 µg) immunoprecipitated with rabbit polyclonal anti-IgG (10 µg); lane 5, shows recombinant LCF incubated with rsCD4 and immunoprecipitated with monoclonal anti-CD4 (10 g); lane 6, shows recombinant LCF incubated with rsCD4 and immunoprecipitated with monoclonal anti-CD8 antibody (10 µg); and lane 7, shows rsCD4 (10 µg) incubated with monoclonal anti-CD8 antibody.

FIG. 5 shows a dose response curve for recombinant LCF induced chemotaxis of human peripheral blood T lymphocytes. In FIG. 5, an asterisk (*) represents statistical significance at p<0.05 (using a Student's T test from control cell migration).

FIG. 6 shows recombinant LCF-induced chemotaxis in murine T cell hybridoma cells. Murine cell lines expressing either wild-type CD4 (13.13), truncated CD4 (delta-13), or mock infected cells lacking CD4 expression (155.16) were stimulated by recombinant LCF ($10^{-9}$M) (open bars) or 2C11 antibody (10 µg/ml) (striped horizontal bars) and the migratory response quantitated. Cells stimulated by recombinant LCF in the presence of a fold excess of anti-CD4 Fab fragments (10 µg/ml) are also shown (solid bars). Cell migration is expressed as mean of ten high power fields +/–S.D. Migration which was significantly different (p<0.05 by Student's T test) from control cell migration (designated as 100%) is indicated by asterisks.

FIG. 7 shows the specificity of recombinant LCF for CD4+ human T cells using FACs analysis. Two×$10^6$ human T lymphocytes were cultured for 24 and 48 h in the presence of $10^{-8}$M recombinant LCF. Cells double-labelled with phycoerythrin-conjugated anti-CD4 antibody and fluoresceinconjugated anti-IL-2R antibody were analyzed on a Becton Dickinson FACscan flow cytometer. Recombinant LCF induced an increase in CD4+/IL-2R+ cells from a control level of 3% (top panel) to 17% (bottom panel) by 48 h. The 24h time point demonstrated an increase in 9% of the cells. At no time did CD4 - cells show an increase in IL-2R expression. This is a representative FACs analysis of three different experiments. Other experiments demonstrated increases in IL-2R+cells at the 48 h time point in 15% and 19% of the cells.

FIG. 8A and FIG. 8B show the aggregation of recombinant LCF under physiological conditions. FIG. 8A shows a molecular sieve HPLC of $^{35}$S-labelled recombinant LCF (run in phosphate buffered saline, pH 8.0). Fractions were collected and analyzed by scintillation counting (open squares). Parallel samples were collected and assayed for the induction of lymphocyte chemotaxis (solid squares). FIG. 8B, lane A and lane B show an autoradiogram of the peak fraction for both radioactivity and cell migration (fraction 13 shown in FIG. 8A) and the second peak of radioactivity which had no corresponding chemoattractant activity (fraction 17 shown in FIG. 8A) after separation by SDS-PAGE, respectively.

FIG. 9 shows a hydrophilicity plot of recombinant LCF predicted by the method of Kyte and Doolittle (Kyte et al., J. Molec. Bio. 157:105–132 (1982)). Peptides were synthesized and rabbit anti-peptide specific anti-sera were generated to four major hydrophilic regions designated by A,B, C,D.

FIG. 10 shows induced chemotaxis of human T lymphocytes by concentrated BAL fluid from normal individuals. Fifty milliliters of BAL fluid was concentrated fold and then assayed diluted 1:1 in phosphate buffered saline in a microchemotaxis chamber. The data is expressed as a percent of random cell migration in the presence of PBS alone (normalized to 100% in all experiments, for these experiments control migration averaged 14.3 cells/hpf). Each BAL fluid was assayed three times, with the asterisks denoting migration statistically different from control cell migration (p<0.05).

FIG. 11 shows the induced migration of peripheral T cells by concentrated BAL fluids from asthmatics following either saline (solid bars) or specific antigen (hatched bars) challenge. The BAL fluids were obtained 6 hrs after challenge and concentrated 100 fold prior to assaying. Each BAL fluid was assayed three times with the asterisks denoting cell migration which was statistically different from control cell migration (p<0.05). For these experiments control migration averaged 12.5 cells/hpf.

FIG. 12 shows the blocking effect of a panel of anti-cytokine antibodies on the induction of peripheral T cell migration by BAL fluids. Positive BAL samples, as determined in FIG. 11, were reassessed for the induction of T cell migration (as shown in panel a) either alone (solid bars ), in the presence of anti-LCF polyclonal antibody (shaded bars), or with anti-MIP1α polyclonal antibody (left hatched bars). Panel (b) shows BALs alone (solid bars), with anti-IL-8 polyclonal antibody (stippled bars), or anti-RANTES monoclonal antibody (horizontal bars). All antibodies were used at a concentration sufficient to neutralize bioactivity from 50 ng/ml of protein. The experiment was conducted three different times and the asterisks denotes cell migration statistically different from cell migration induced by the same BAL sample assayed alone (p<0.05). Control migration in these experiments averaged 15 cells/hpf.

FIG. 13 shows the blocking of BAL fluid-induced T cell migration by anti-LCF, anti-MIP1α or a combination of the two antibodies. Induction of cell migation was assessed for BAL samples incubated either alone (solid bars), in the presence of anti-MIP1α antibody (left hatched bars), in the presence of anti-LCF antibody (shaded bars), or in a combination of the two antibodies (horizontal bars). Antibodies were used at concentrations sufficient to neutralize bioactivity from 50 ng/ml of specific protein. The data is expressed as percent of control cell migration, with asterisks denoting inhibition of migration which was statistically different from BAL-induced cell migration in the absence of blocking antibodies (p<0.05). Control migration in these experiments averaged 13.8 cells/hpf.

LCF Polypeptides

Figure 3A:

LCF polypeptides according to the invention include the full-length LCF polypeptide (as described in FIG. 2, SEQ ID NO: 1). Such polypeptides may be derived from any source. These polypeptides are used, e.g. to screen for antagonists which disrupt a LCF:CD4 receptor interaction or an LCF-mediated physiological response (see below). LCF fragments or analogs may also be useful candidate antagonists of LCF:CD4 receptor activity. The efficacy of a LCF fragment or analog antagonist is dependent upon its ability to interact with CD4; such an interaction may be readily assayed using any number of standard binding methods and LCF-mediated CD4 receptor functional assays (e.g., those described below). Polypeptides of the invention also include any fragment or analog capable of interacting with the CD4 receptor and mediating the LCF biological cascade, i.e. LCF agonists.

Specific LCF polypeptide fragments of interest include any portion of the LCF polypeptide which are capable of interaction with CD4 receptor, e.g., all or part of the N-terminus or e.g., a hydrophilic domain. Based on the hydrophilicity analysis (see FIG. 9) and biologic inhibition data, other likely candidates include without limitation, the four hydrophilic regions, A, B, C and D (see FIG. 5) and the FEAW (Phe, Glu, Ala, Trp) sequence from amino acids 96-99 of LCF (FIG. 2 and SEQ ID NO: 1). Such fragments may be useful as agonists or antagonists (as described above), and are also useful as immunogens for producing antibodies which neutralize the activity of LCF; see infra).

Alternatively, from the primary amino acid sequence the secondary protein structure and, therefore, the domains of LCF may be deduced semi-empirically using any standard hydrophobicity/hydrophilicity calculation, e.g., the Chou-Fasman method (see,e.g., Chou and Fasman, Ann. Rev. Biochem. 47:251, 1978). Hydrophilic domains present themselves as strong candidates for antigenicity and hydrophobic regions for binding domains, and therefore, useful antagonists or agonists.

Candidate fragments (e.g., all or part of Domains A or D; see, FIG. 9) are then tested for interaction with CD4 receptor and their ability to induce an LCF-mediated physiological response, i.e., serve as LCF agonists, by assays described herein. Fragments are also tested for their ability to antagonize the interaction between LCF and CD4 using the assays described herein. Analogs of useful LCF fragments (as described above) may also be produced and tested for efficacy as screening components or antagonists (using the assays described herein); such analogs are also considered to be useful in the invention.

There now follows a description of the cloning and characterization of a human LCF cDNA useful in the instant invention. This example is provided for the purpose of illustrating the invention, and should not be construed as limiting.

Isolation of Human LCF cDNA

The human LCF gene was isolated as follows.

Figure 1:
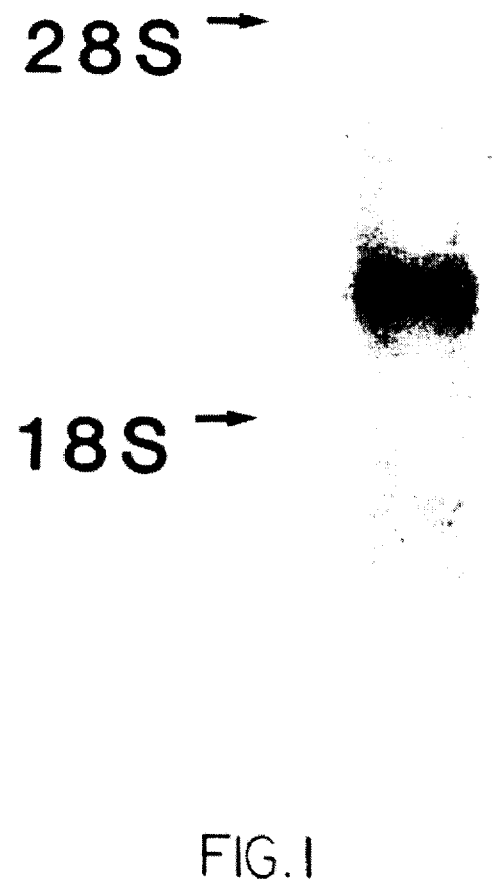

A cDNA library from mitogen-stimulated human peripheral blood mononuclear cells (PBMC) was ligated into the COS cell expression vector pXM (Wong et al., Science 228:801–815, 1985). Supernatants from cells transfected with pooled plasmids were screened for lymphocyte chemoattractant activity using a modified Boyden chamber assay (Cruikshank et al., J. Immunol. 128:2569–2574, 1982). Supernatants collected 24h after transfection were placed in bottom wells of microchambers. The migration of human T cells through 8 μm nitrocellulose filters in response to the presence of these supernatants was determined, compared to supernatant of mock (vector only) transfected COS cells. Supernatants with chemoattractant activity were further screened for the capacity to induce IL-2R expression on resting T-cells by FACs analysis of cells incubated with fluorescein-conjugated anti-Tac antibody, and for the ability of Fab fragments of monoclonal OKT4 antibody to block this induction (Cruikshank et al., J. Immunol. 138:3817–3723, 1987). Seven different subclonings were screened, approximately 200 clones per supernatant in original supernatants that were subcloned were found to be positive. Next, the supernatants were sequentially subcloned and diluted until one clone per supernatant was obtained. The criteria established for the presence of LCF-containing supernatant included a positive response for both assays and, in addition, that the activity could be blocked by coincubation with Fab fragments generated from OKT4 antibodies (Ortho Pharmac, Raritan, N. J.). A single clone (LCF-7) with these characteristics was isolated and both strands were sequenced by the dideoxynucleotide chain termination method (Sanger et al., Proc. Natl. Acad. Sci. U.S.A. 74:5463–5467, 1977). Sequence analysis and northern blotting (FIG. 1) indicated that the LCF-7 cDNA was not full-length (corresponding to nucleotide 441 to 1450 of the indicated sequence). Then, the LCF-7 cDNA was used to probe a second mitogen-stimulated human PBMC cDNA library ligated into bacteriophage lambda ZAP. 125,000 plaques were screened with full length LCF-7. Upon screening, three clones were isolated ranging in size from 0.6- to 2.2-kb. The largest clone was sequenced on both strands (see FIG. 2; SEQ ID NO: 2). Partial sequencing of two shorter clones revealed that they were identical to LCF-A, but incompletely extended in the 5'direction.

As described above, LCF cDNA was isolated by screening a COS cell expression library of mitogen-stimulated human peripheral blood mononuclear cells (PMBC). Supernatants were assessed for the presence of LCF by the induction of human CD4+ T cell chemotaxis and cell cycle changes as determined by upregulations of IL-2 receptors (IL-2R) (Cruikshank et al., J. Immunol. 138:3817–3823, 1987). Following four rounds of screening, a positive supernatant from a single clone of 1-kb was identified. The LCF cDNA was used to probe a northern blot of total RNA isolated from human T cells (FIG. 1). A single band of 2.2-kb was detected. In order to isolate a full length clone the 1-kb LCF cDNA was used to probe a second mitogen-stimulated human PBMC cDNA library. Three clones were isolated, and the sequence of the largest clone is shown in FIG. 2 and SEQ ID NO: 2.

Within the LCF cDNA there is an open reading frame of 393 base pairs extending from nucleotide 783 to 1176 that codes for a 130 residue protein with a predicted molecular mass of 13,385 daltons. The methionine at nucleotide 783 is in good context for initiation by Fickett analysis (Fickett, *Nucleic Acids Res.* 10:5303–5318, 1982). The only other possible initiation site lies downstream and is in-frame, representing residue 38 of the predicted amino acid sequence. There is one potential N-linked glycosylation site on the serine located five residues after the start methionine. While previous work suggests that native LCF is a secreted cytokine (Cruikshank et al., *J. Immunol.* 128:2569–2574, 1982), in the predicted amino acid sequence there is no consensus hydrophobic signal sequence; however, nor is there a potential transmembrane domain. While most secreted cytokines contain a signal sequence, the absence of a signal sequence has been reported for both secreted IL-1α and IL-1α. Similarly searches of the Genbank nucleic acid and protein data bases failed to find any related sequences. DNA and protein homology searches were conducted using the programs FASTA, SEARCH, and BLAST in the Genbank and PIR databases.

RNA Isolation and Northern Analysis

Human peripheral blood mononuclear cells (PBMC) were prepared by Ficoll-Paque density centrifugation as previously described (Cruikshank et al., *J. Immunol.* 138:3817–3823, 1987; Cruikshank et al., *J. Immunol.* 146:2928–2934, 1991). The T lymphocyte population was purified by plastic adherence followed by nylon wool adherence and finally by sheep erythrocyte rosetting and centrifugation. Cells recovered from the pellet were >99% T lymphocytes as determined by fluorescent analysis. Monocytes were purified from PBMC using sheep erythrocyte rosetting to deplete T lymphocytes, followed by plastic adherence of the cells remaining in the supernatant after the rosetting step. Adherent cells recovered from the plastic were >92% monocytes by fluorescence analysis. All cells were lysed with cold 4 M guanidinium isothiocyanate and RNA was isolated by CsCl centrifugation (Ausubel et al., *Current Protocols in Molecular Biology*, John Wiley & Sons, New York, 1989). Ten μg of RNA from each sample was loaded on a 1% agarose-formaldehyde gel for electrophoresis, and blotted onto nylon membrane. A cDNA probe from a 704 bp Pst I fragment of recombinant LCF-7 was [$^{32}$P]dCTP-labeled by the random primer method (Feinberg et al., *Anal. Biochem.* 132:613, 1983) and the blot was hybridized with 1×10$^6$ cpm/ml for 24 hr. After hybridization the blot was washed with 0.2×SSC (30 mM NaCl, 3 mM sodium citrate, 0.05% sodium pyrophosphate, 0.1% sodium lauryl sarcosine) at 56° C., and hybridization was visualized by autoradiography. As shown in FIG. 1, the probe hybridized specifically to a lymphocyte RNA of approximately 2.2 kilobases. This confirmed that LCF was expressed in T lymphocytes and indicated that the clone was full-length.

LCF Polypeptide Expression and Synthesis

Polypeptides according to the invention may be produced by transformation of a suitable host cell with all or part of an LCF-encoding cDNA fragment (e.g., the cDNA described above) in a suitable expression vehicle.

Those skilled in the field of molecular biology will understand that any of a wide variety of expression systems may be used to provide the recombinant LCF protein. The precise host cell used is not critical to the invention. The LCF polypeptide may be produced in a prokaryotic host (e.g., *E. coli*), or in a eukaryotic host (e.g., *S. cerevisiae* or mammalian cells, e.g., COS1, NIH3T3, and JEG3 cells, or in the cells of an arthropod, e.g. *Spodoptera frugiperda* (SF9) cells). Such cells are available from a wide range of sources (e.g., the American Type Culture Collection, Rockland, M.d.; also see, e.g., Ausubel et al., supra). The method of transfection and the choice of expression vehicle will depend on the host system selected. Transformation and transfection methods are described, e.g., in Ausubel et al., supra; expression vehicles may be chosen from those provided, e.g., in Cloning Vectors: *A Laboratory Manual* (P. H. Pouwels et al., 1985, Supp. 1987).

Figure 3B:
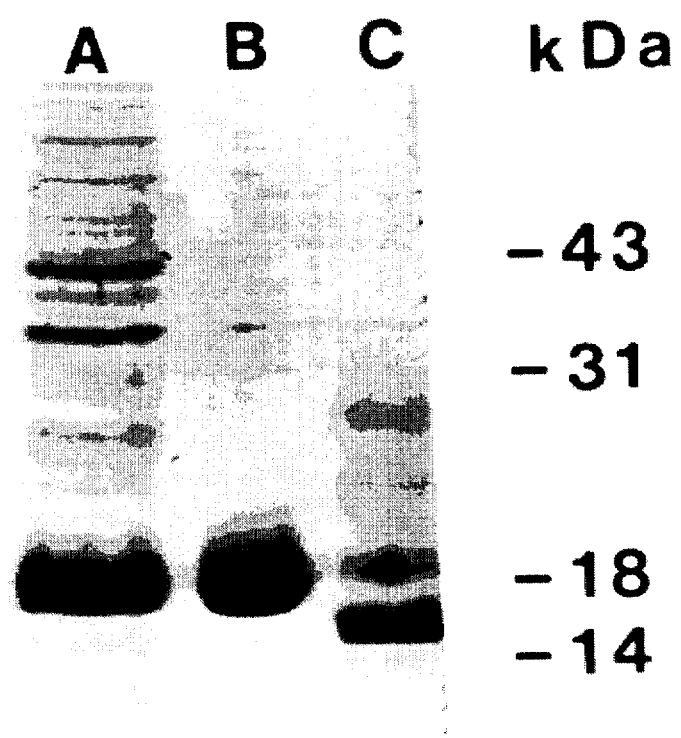

One preferred LCF expression system is a prokaryotic expression system as described by Ausubel et al. (supra). Thus, a DNA fragment containing the LCF cDNA open reading frame with flanking BamH1 and Nde1 restriction sites was generated by PCR according to standard methods and ligated into the *E. coli* expression vector pT-16b (Novagen). This plasmid, pET-166-ICF, was then used to transform *E. coli* JM109. In order to stimulate the production of recombinant LCF the transformed bacterial were stimulated with IPTG, grown in culture media and subsequently lysed. Recombinant protein was isolated by metal chelation chromatography according the well known methods (see, e.g., Studier *Meth. Enzymol.* 185:60–89, 1990). Recombinant LCF was then subjected to SDS-PAGE (FIG. 3A) and blotted to Problott transfer filters (Applied Biosystems). A prominent band found at an apparent molecular weight of 17.5 kDa was excised and subjected to N-terminal amino acid sequencing according to standard techniques. Twenty-five amino acid residues at the N-terminus of the recombinant LCF were sequenced and were found to be identical to the predicted amino acid sequence shown in FIG. 2 (SEQ ID NO: 1). While the SDS-PAGE mass of 17.5 kDa is larger than the expected 13.4 kDa based on nucleotide sequence, it is identical to the migration pattern of $^{35}$S-labeled in vitro translated protein (FIG. 3B). The discrepancy in mass determined by SDS-PAGE-from the predicted sequence may be due to aberrant migration of recombinant LCF in the SDS acrylamide gel system.

Another preferred LCF expression system is a baculovirus expression system as described by Ausubel et al. (supra). DNA encoding an LCF polypeptide is inserted into an appropriate transfer vector, e.g., pVL1392 (Invitrogen Corp., San Diego, Calif.). Next, the vector is co-transfected with wild type baculovirus genomic DNA into *Spodoptera frugiperda* (SF9) cells (ATTC Accession No: CRL 1711) and recombinant viruses are isolated by standard techniques, e.g., see Ausubel et al. (supra). Recombinant LCF produced in a baculovirus system was found to synthesize a protein with an apparent molecular weight of 17.5 kDa which is similar to the protein synthesized using the *E. cole* expression system shown in FIG. 3A and FIG. 3B. Sequencing of the first five N-terminal amino acid residues of the baculovirus recombinant LCF was performed. The sequences were found to be identical to the predicted amino acid sequence shown in FIG. 2 (SEQ. ID No.: 1) with a methionine at position 783 as the initiation site.

Alternatively, an LCF polypeptide may be produced by a stably-transfected mammalian cell line. A number of vectors suitable for stable transfection of mammalian cells are available to the public, e.g., see Pouwels et al. (supra); methods for constructing such cell lines are also publicly available, e.g., see Ausubel et al. (supra). In one example, cDNA encoding the LCF polypeptide is cloned into an expression vector which includes the dihydrofolate reductase (DHFR) gene. Integration of the plasmid and, therefore, the LCF-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) as described in Ausubel et al. (supra). Any of the host cells described above or, preferably, a DHFR-deficient CHO cell line (e.g., CHO DHFR-cells, ATCC Accession No. CRL 9096) are among the host cells preferred for DHFR selection of a stably-transfected cell line or DHFR-mediated gene amplification.

Once the recombinant LCF polypeptide is expressed, it is isolated, e.g., by using affinity chromatography. In a working example, a CD4 affinity column was prepared by coupling recombinant soluble CD4 (rsCD4) to CNBr Sepharose 4B according to previously described methods (see, e.g., Cruikshank et al., Journal of Immunology 1991). Thus, 100µg rsCD4 was covalently conjugated to a CNBr activated Sepharose 4B (Pharmacia, Piscataway, N. J.). Next, an in vitro RNA transcript of LCF was generated and used for in vitro translation with rabbit reticulocyte lysate in the presence of [$^{35}$S] methionine according to standard methods. $^{35}$S-labeled in vitro LCF was applied to the column for 3hr at 37° C. at which time the column was extensively washed with wash buffer (0.01 M Tris-Cl, pH 8.0, 0.14 M NaCl, 0.025% NaN$_3$, 0.5% Triton X-100, 0.5% sodium deoxycholate). LCF was eluted with a triethanolamine solution (50 mM triethanolamine, pH 11, 0.1% Triton X-100, 0.15 M NaCl) into tubes containing 1M Tris-Cl, pH 6.7 and analyzed.

Once isolated, the recombinant protein can, if desired, be further purified, e.g., by high performance liquid chromatography. These general techniques of polypeptide expression and purification can also be used to produce and isolate useful LCF fragments or analogs (as described below). Furthermore, the eluate may then, if desired, be run on a SDS-PAGE and visualized by autoradiography (see, e.g., the results from the above experiment presented in FIG. 3B).

Finally, LCF polypeptides, particularly short LCF fragments, can be produced by chemical synthesis (e.g., by the method described in *Solid Phase Peptide Synthesis*, 1984, 2nd ed. , Stewart and Young, eds., Pierce Chemical Co., Rockford, Ill.).

Assays for LCF Binding and Function

Useful LCF polypeptide fragments or analogs in the invention are those which interact with CD4 receptor, e.g., LCF agonists or antagonists. Such an interaction may be detected by an in vitro binding assay (as described infra) followed by functional analysis. Thus, the fragments or analogs thereof may also be assayed functionally, i.e., for its ability to bind a CD4 receptor and to induce the migration of T4+lymphocytes, monocytes, eosinophils and the like (as described infra). These assays include, as components, LCF (or a suitable LCF fragment or analog thereof) and recombinant soluble CD4 receptor (rsCD4) or CD4 receptor-bearing cell, e.g., an eosinophil, configured to permit detection of binding. Thus, the invention includes methods for screening compounds useful as LCF agonists.

One such assay method is as follows. Full-length LCF polypeptide (fragment or analog thereof) is produced as described supra. CD4 receptor component is produced either as a recombinant soluble component or is produced as a membrane component by a cell, e.g., a T lymphocyte, monocyte or eosinophil.

In vitro assays to determine the extent of LCF (fragment or analog thereof) binding to rsCD4 or CD4 receptor-bearing cells is then performed. For example, a whole cell assay is preferably performed by fixing the cell expressing the CD4 receptor, e.g, eosinophils, to a solid substrate (e.g., a test tube, or a microtiter well) by means well known to those in the art (see, e.g., Ausubel et al. supra) and presenting labelled LCF polypeptide (e.g., $^{125}$I-labelled LCF). Labelling of LCF, e.g., with $^{125}$I, is performed according to standard techniques known in the art. Binding is assayed by the detection label in association with the receptor component (and, therefore, in association with the solid substrate and CD4 receptor) by techniques well known in the art.

The assay format may be any of a number of suitable formats for detecting suitable binding, such as a radioimmunoassay format (see, e.g., Ausubel et al., supra). Preferably, cells bearing CD4 receptor are immobilized on a solid substrate (e.g., the well of a microtiter plate) and reacted with LCF polypeptide which is detectably labelled, e.g., with a radiolabel such as $^{125}$I or an enzyme which can be assayed, e.g., alkaline phosphatase or horseradish peroxidase. Thus, $^{125}$I-labelled LCF is bound to the cells and assayed for specific activity; specific binding is determined by comparison with binding assays performed in the presence of excess unlabelled LCF polypeptide.

Alternatively, LCF polypeptide (fragment or analog thereof) may be adhered to the solid substrate (e.g., to a microtiter plate using methods similar to those for adhering cells for an ELISA assay; Ausubel et al. supra) and the ability of labelled rsCD4 receptor to bind LCF can be used to detect specific rsCD4 receptor binding to the immobilized LCF.

Figure 4:
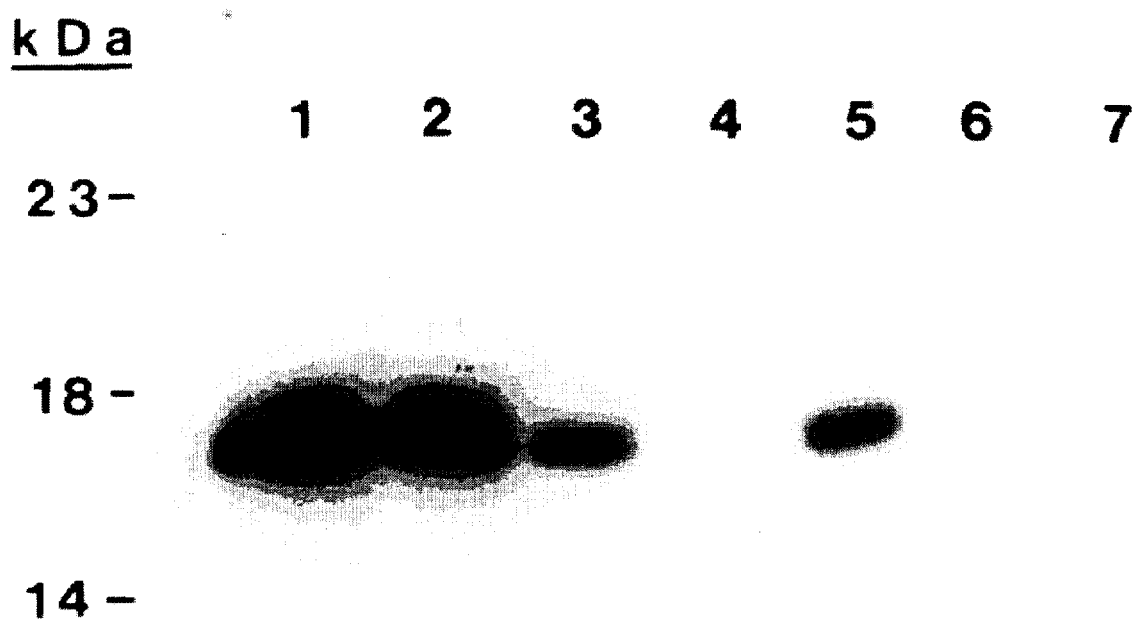

There now follows an example demonstrating still another method useful for analyzing the LCF:CD4 interaction. In this method recombinant LCF-containing *E. coli* crude supernatant was incubated with 10 µg of rsCD4 for 1 h at 40° C. Next, the recombinant LCF-CD4 complex was added to protein A Sepharose beads which had been incubated with 1µg rabbit anti-CD4 polyclonal antibody and washed with a suitable buffer. The mixture was then incubated for 2h at 40° C., washed four times with TSB (0.01M Tris, (pH 8.0), 0.14M NaCl, 0.025% NaN$_3$) prior to running on a 15% SDS-polyacrylamide gel system. Protein separated on the SDS-gel was then transferred to Problott transfer filters and probed using rabbit anti-peptide D antibody (1:200 dilution) (also see section infra anti-LCF Antibodies) followed by goat anti-rabbit $^{125}$I-IgG antibody. The results of this experiment are presented in FIG. 4. As shown in FIG. 4, there is a detectable specific physical interaction between recombinant LCF and rsCD4.

Figure 5:
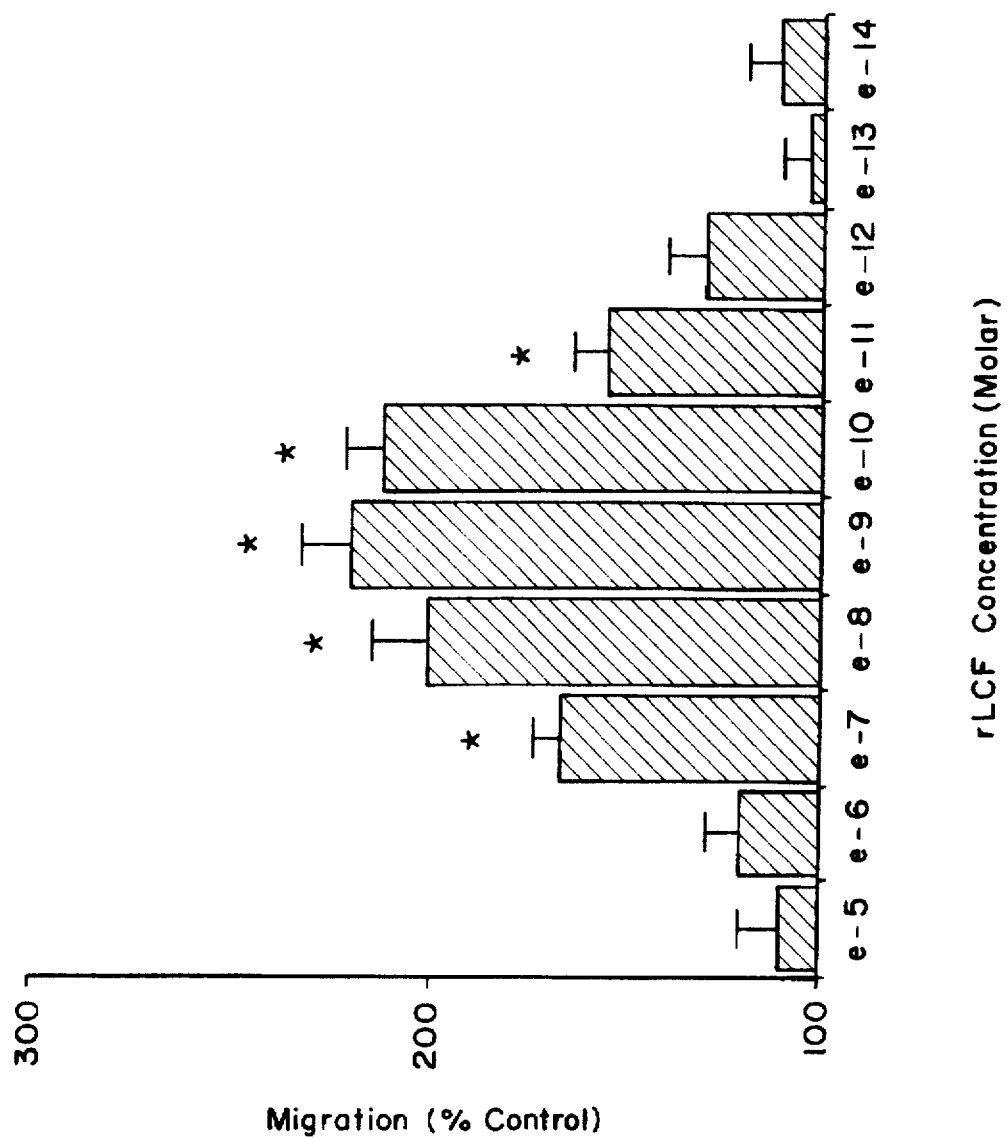

LCF polypeptide (or fragment or analog thereof) may also be assayed functionally for its ability to mediate migration of CD4 + lymphocytes, monocytes, eosinophils and the like. Migration assays may be employed using any suitable cell, e.g., T lymphocytes, monocytes or eosinophils as described in (Cruikshank et al., 1987, *J. Immunol.* 128: 2569–2571; Rand et al., 1992, *J. Exp. Med.* 173:1521–1528) follows. For example, recombinant LCF synthesized in an expression system, e.g., *E. coli* or baculovirus expression systems (as described supra), can be assayed for the ability to induce cell migration. In one working example, murine cell chemotaxis was performed using a modified Boyden chemotaxis chamber (Cruikshank et al, *J. Immunol.* 128: 2569–2571). The cells were suspended in RPMI 1640 containing 10% FBS at a concentration of 5×10$^6$ cells/ml. A 12 µm nitrocellulose membrane was used and the cells were incubated for 4 h. Next, the membranes were stained with hematoxylin and dehydrated using sequential washing with ethanol, propanol, and finally xylene to clarify the filters and allow for cell counting by light microscopy. Cell migration was quantitated by counting the number of cells which had migrated beyond 50 μm. All counts were compared with control cell (unstimulated) migration which was always normalized to 100%. In addition, all samples were performed in duplicate and five high-powered fields were counted for each duplicate. FIG. 5 shows a representative dose response curve for protein generated from the *E. coli* expression system (supra). As indicated from the dose response curve, maximal migration was induced with a concentration of recombinant LCF at $10^{-9}$M, and $ED_{50}$ of $10^{-11}$M. Statistics were performed using Student's T Test (or analysis of variance modifications when data from multiple experiments were pooled) and counts statistically different from control cell migration ($p<0.05$) are designated by an asterisk. Similar results were obtained when baculovirus-produced LCF was substituted for *E. coli*-produced LCF.

Figure 6:
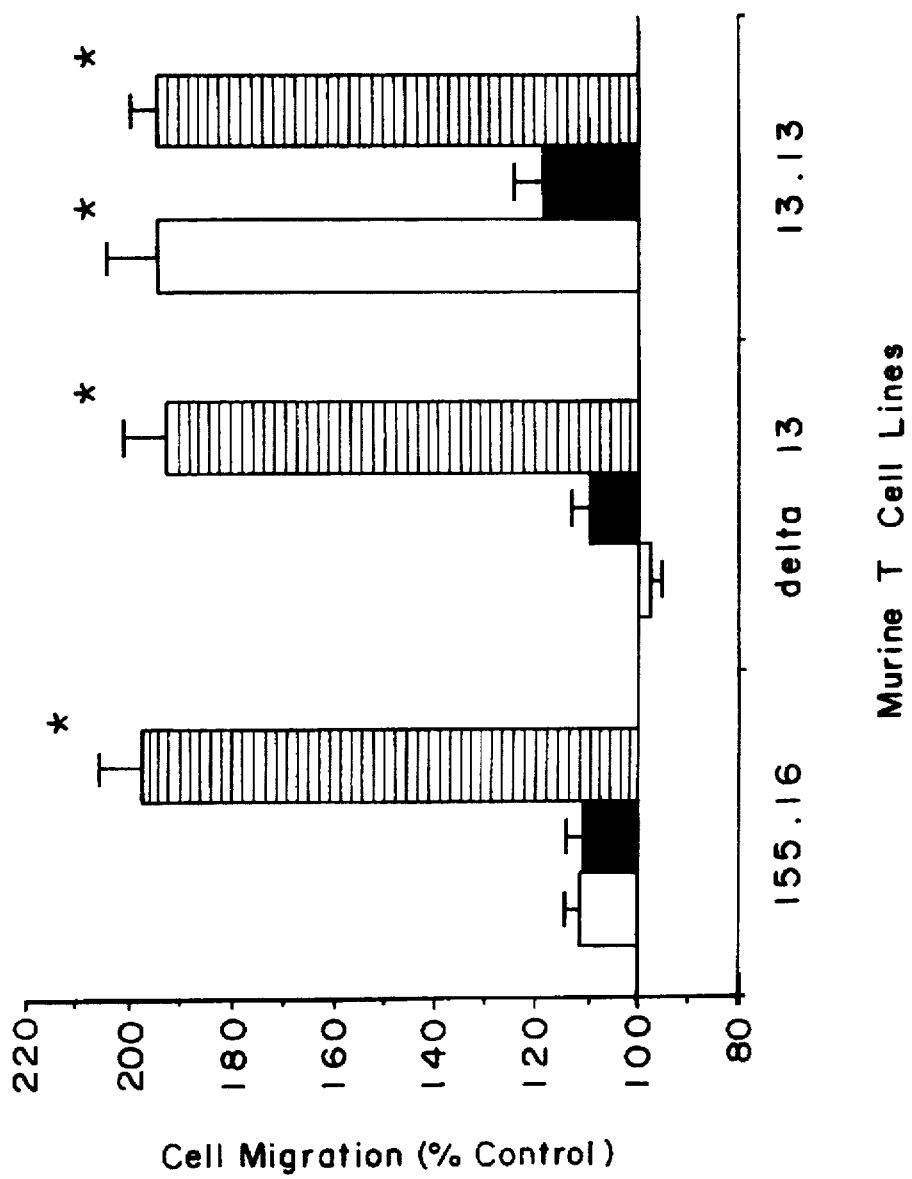

In order to demonstrate that this physical association between recombinant proteins in solution corresponds to a specific functional association between recombinant LCF and cell surface CD4 the effects of recombinant LCF on murine T cell hybridoma cell lines expressing either full-length or truncated human CD4 was examined (Sleckman et al., 1987, 1988). Three cell lines were employed: a mock infected cell line which lacked expression of CD4; a cell line expressing intact (wild type) CD4; and a cell line expressing truncated CD4 (delta 13) in which the 31 most distal residues of the cytoplasmic tail of CD4 have been deleted. The cell lines expressing either intact CD4 or delta 13 CD4 were chosen for their comparable levels of CD4. As shown in FIG. 6 cells which expressed intact CD4 migrated in response to recombinant LCF stimulation. Cells either lacking CD4 or expressing delta 13 CD4 were unresponsive to recombinant LCF. These cells were responsive to murine T cell receptor-stimulated migration as the antibody 2C11 induced migratory responses of 198%+4% and 192%+3% for the mock transfected and delta 13 CD4 cell lines respectively (FIG. 6). These studies demonstrate that CD4 must be expressed for LCF-induced cell motile responsiveness and that the cytoplasmic tail is required.

Figure 7:
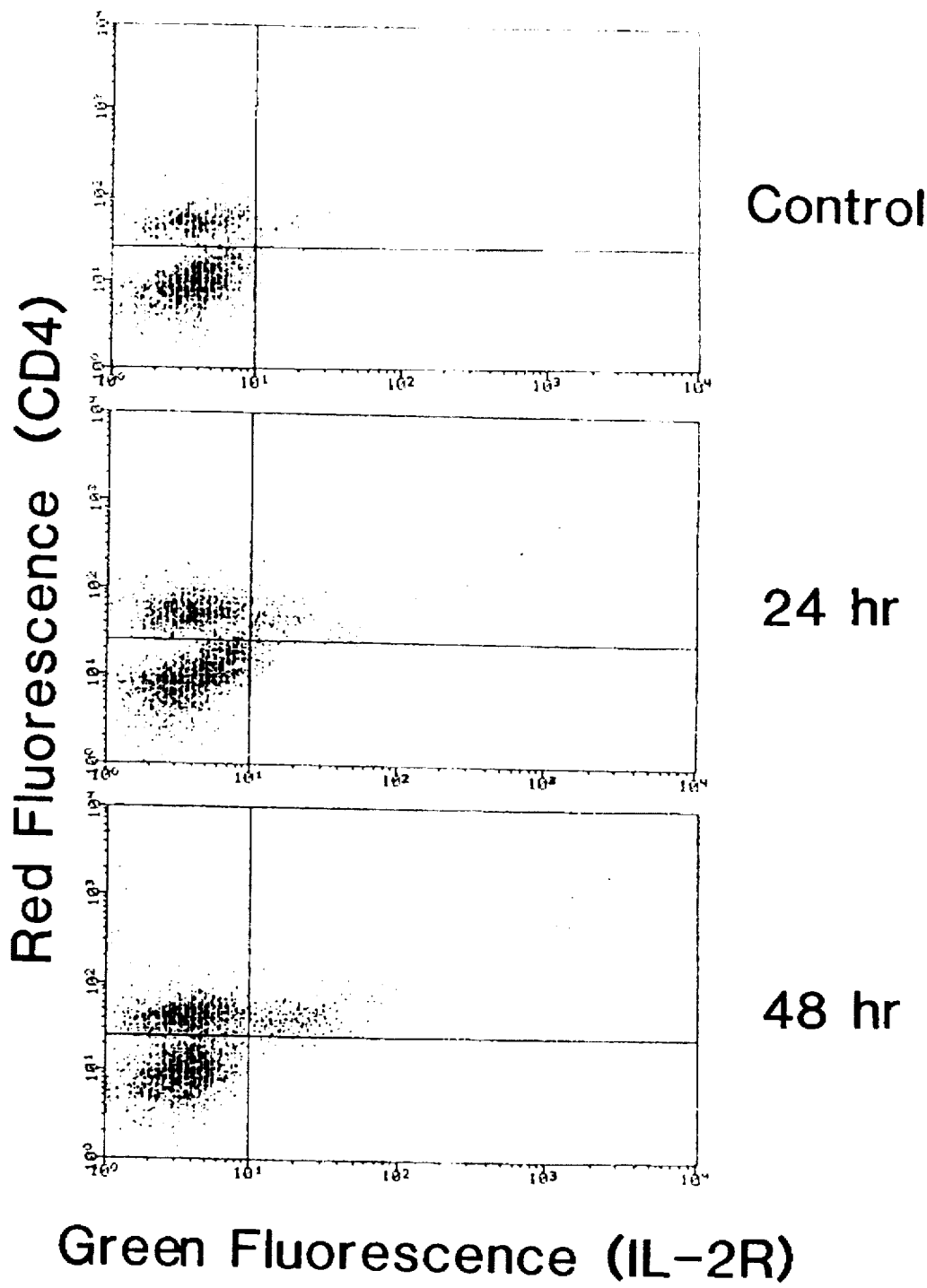

CD4 specificity for LCF stimulation in human T cells was demonstrated using the expression of IL-2R to identify LCF responsive cells. Mixed T cells were cultured in the presence of recombinant LCF ($10^{-8}$M) for 24 and 48 hrs at which time the cells were labeled for their expression of both CD4 and IL-2R. As shown in FIG. 7, only cells which were $CD4^+$ demonstrated an increase in surface expressed IL-2R. In this particular experiment an increase in IL-2R was observed for 17% of the $CD4^+$ cells. This indicates not only LCF specificity for $CD4^+$ cells, but also suggests that recombinant LCF acts only on a subset of $CD4^+$ cells.

Figure 8A:
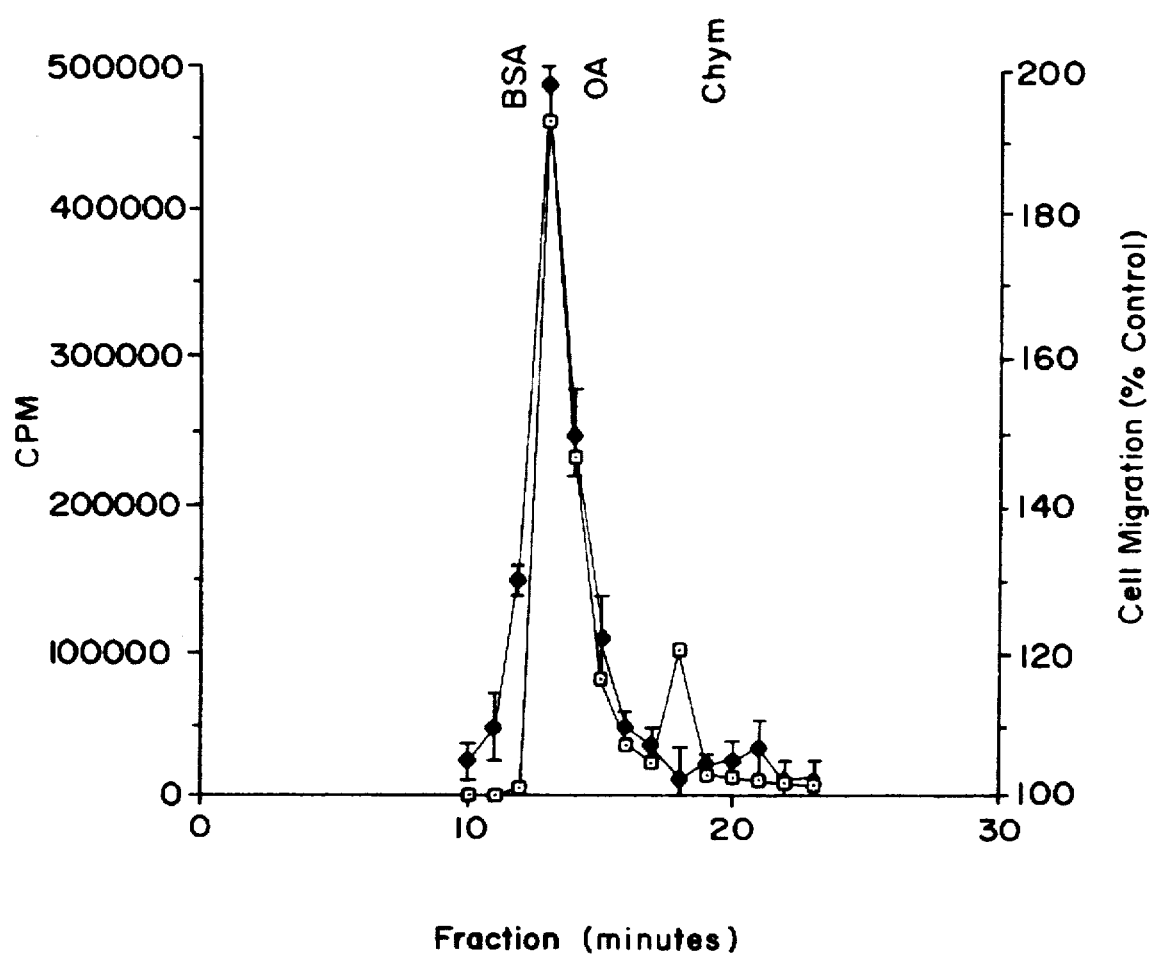
Figure 8B:
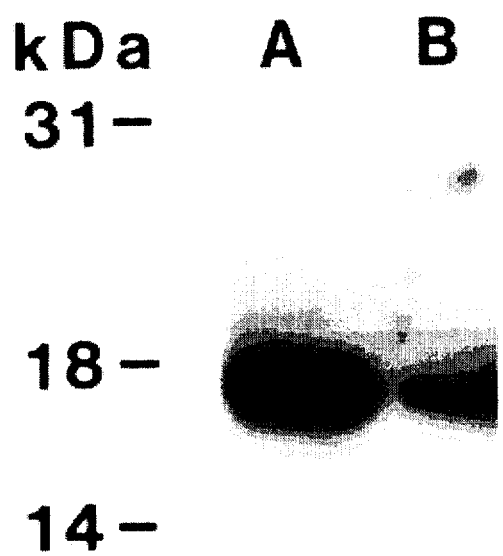

Finally, molecular weight sieve chromatography of recombinant LCF shows that most chemoattractant activity elutes in the 50–60 kDa region. This peak of chemoattractant activity corresponds to the elution profile of $^{35}$S-labeled recombinant LCF subjected to identical chromatography as shown in FIG. 8A and FIG. 8B. A small peak of radioactivity was present with no corresponding chemoactivity in the 14–18 kDa region. The peak fraction for both chemotaxis and radioactivity (fraction 13) and the fraction containing only radioactivity (fraction 17) were applied to SDS-PAGE and subjected to autoradiography. The LCF proteins from each fraction appeared as single bands at 17.5 kDa (FIG. 8B). These data suggest that under physiologic conditions LCF exists predominantly as a non-covalently linked multimer, but some LCF may exist as monomers. The multimeric form, however, is believed to possess chemoattractant activity.

Screening For Compounds that Inhibit LCF:CD4 Interaction

As discussed above, one aspect of the invention features screening for compounds that antagonize the interaction between LCF and CD4 receptor, thereby preventing or reducing the cascade of events that are mediated by that interaction. Chemical antagonists to LCF which bind to LCF or LCF/CD4 receptor or CD4 receptor without triggering a response are used to reduce, attenuate or interfere with the effects of LCF or cross-linked LCF agonists or biologically active LCF polypeptide fragments or analogs thereof which act to stimulate or activate LCF-mediated events of the immune response and inflammation. Thus, the invention provides for methods to screen for such useful compounds. These antagonists include, without limitation, e.g., cross-linked LCF, synthetic LCF, anti-LCF antibodies, or other drugs, e.g. organic compounds.

Thus, LCF polypeptide can be used to prepare compounds that tend to neutralize or impede its activity. For example, one approach pertains to identification of the active sites of LCF, followed by the alteration of those sites of the LCF amino acid sequence by substitution of amino acids within the active site by other amino acids, so that the peptide does not lose its binding affinity for the CD4 receptor, but upon binding is unable to promote activity, and thereby blocks the effect of LCF. LCF activity may also be blocked, attenuated, or interfered with by using antibodies, e.g., monoclonal, or chemical antagonists to LCF. These chemical antagonists include any organic compounds, or any of the other aforementioned compounds, which can be assayed or screened for their ability to interfere with LCF:CD4 mediate events by the methods that follow.

The elements of the screen are LCF polypeptide (or a suitable fragment or analog thereof) and rsCD4 or, a CD4 receptor expressing cell, e.g., $CD4^+$ lymphocyte, monocyte, eosinophil and the like, configured to permit detection of binding. A full-length LCF polypeptide (fragment or analog thereof) and rsCD4 may be produced as described above.

Binding of LCF to its receptor may be assayed by any suitable method (as described above). For example, cells expressing CD4 receptor, e.g., eosinophils, are immobilized on a solid substrate (e.g., the well of a microtiter plate) and reacted with detectably-labelled LCF polypeptide (fragment or analog thereof) as described above. Binding is assayed by the detection label in association with the receptor component (and, therefore, in association with the solid substrate). Binding of labelled full-length recombinant LCF polypeptide to CD4 receptor bearing cells is used as a "control" against which antagonist assays are measured. The antagonist assays involve incubation of the CD4 receptor bearing cells with an appropriate amount of candidate antagonist, e.g., an antibody or an organic compound. To this mix, an equivalent amount of labelled LCF is added. An antagonist useful in the invention interferes with labelled-LCF binding to the immobilized receptor-bearing cells. Alternatively, an antagonist may bind but not activate a biological response.

Subsequently, an antagonist, if desired, may be tested for its ability to interfere with LCF function, i.e., to specifically interfere with labelled LCF binding without resulting in signal transduction normally mediated by a full-length LCF polypeptide.

Appropriate candidate antagonists include e.g., the polypeptides FEAW (Phe-Glu-Ala-Trp at amino acids 96–99) and RKSLQSKETTAAGDS (Arg-Lys-Ser-Leu-Gln-Ser-Lys-Glu-Thr-Thr-Ala-Ala-Gly-Asp-Ser at amino acids 116-130) see e.g., SEQ ID No.:1 analogs of LCF, and other peptides as well as nonpeptide compounds, and anti-LCF polypeptide antibodies designed or derived from analysis of LCF/CD4 receptor interaction or the primary structure of LCF.

Anti-LCF Polypeptide Antibodies

Human LCF (or fragments or analogs) may be used to raise antibodies useful in the invention; such polypeptides may be produced by recombinant or peptide synthetic techniques (see, e.g., Solid Phase Peptide Synthesis, supra; Ausubel et al., supra). The peptides may be coupled to a carrier protein such as KLH as described in Ausubel et al., supra. The KLH-peptide is mixed with Freund's adjuvant and injected into guinea pigs, rats, donkeys and like or preferably rabbits. Antibodies may be purified by peptide antigen affinity chromatography.

Figure 9:
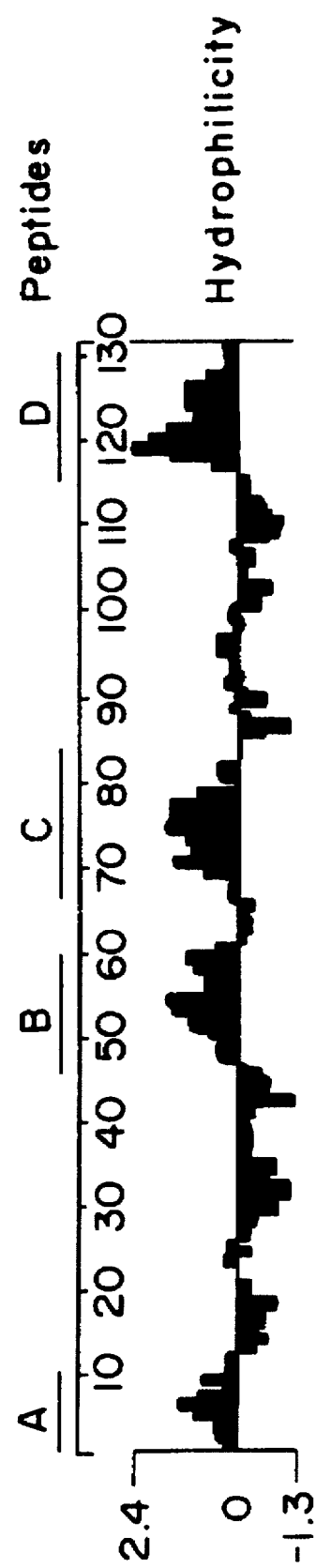

For example, Kyte-Doolittle analysis (Kyte, *J. Molec. Bio.* 157:105-132, 1982) of the predicted amino acid sequence revealed four major hydrophilic regions (FIG. 9). Based on the LCF hydrophilicity plot, rabbit antibodies to synthetic polypeptides of the four major hydrophilic regions from residues 3-11, 47-58, 68-81 and 115-130 (designated in FIG. 9 as A, B, C, D, respectively) were generated. Peptide specific polyclonal antisera were identified by ELISA for each peptide and then purified by protein A sepharose chromatography. In one example demonstrating the utility of such antibodies, it was determined that antibodies generated to region D blocked recombinant LCF ($10^{-9}$M)-induced migration from 194%+7% (mean+S.D., N=4) to 112%+5% in the chemotaxis indicator assay system (described supra). Furthermore, the anti-peptide D antibody was found to be suitable for western blotting and identified the same 17.5 kDa band as was observed following protein staining in FIG. 3A and FIG. 3B.

Alternatively, monoclonal antibodies may be prepared using LCF polypeptides described above and standard hybridoma technology (see, e.g. Kohler et al., *Nature*, 256:495, 1975; Kohler et al., *Eur. J. Immunol.* 6:511, 1976; Kohler et al., *Eur. J. Immunol.*, 6:292, 1976; Hammerling et al., *In Monoclonal Antibodies and T Cell Hybridomas*, Elsevier, N.Y., 1981; Ausubel et al., supra). Thus, in one example, monoclonal antibodies to LCF (fragments or analogs thereof) can be raised in Balb/C or other similar strains of mice by immunization with purified or partially purified preparations of LCF (fragments or analogs thereof). The spleens of these mice can be removed, and their lymphocytes fused to a mouse myeloma cell line. After screening of hybrids by known techniques, a stable hybrid will be isolated that produces antibodies against LCF (fragments or analogs thereof). Such activity can be demonstrated by the ability of the antibody to prevent the binding of radiolabelled LCF (e.g., $^{125}$I-LCF) to the CD4 receptor. The monoclonal antibody can then be examined for its ability to prevent the biological activity of LCF, e.g., cell migration (as discussed above). Once produced, polyclonal or monoclonal antibodies are tested for specific LCF polypeptide recognition by Western blot or immunoprecipitation analysis (by methods described in Ausubel et al., supra). Antibodies which specifically recognize an LCF polypeptide (fragment or analog thereof) are considered to be likely candidates for useful antagonists; or such antibodies may be used, e.g., in an immunoassay to monitor the level of LCF polypeptide produced by a mammal, e.g., a human. Antibodies which antagonize LCF/CD4 receptor binding or LCF mediated CD4 receptor function are considered to be useful antagonists in the invention.

Identification of LCF in Bronchial Alveolar Lavage Fluid (BAL) of Antigen Challenged Asthmatics Below we describe the identification of two lymphocyte chemoattractants present in the BAL of asthmatics by 6 hrs following antigen challenge. One chemoattractant (LCF), a $CD8^+$ cell product, acts exclusively on $CD4^+$ cells, while the second chemoattractant (MIP1$\alpha$), a monocyte product, appears to act on both $CD4^+$ and $CD8^+$ cells. An important finding of these studies is that the chemical stimuli which result in T cell accumulation in the lung in asthma are products of an inflammatory cascade which begins very early following antigen stimulation. Furthermore, we demonstrate that the majority of the lymphocyte chemoattractant activity found in BAL fluid following antigen challenge is attributable to LCF. This example is intended to illustrate, not limit, the invention.

Materials and Methods

Subjects.

Nine normal subjects (Table 1) and seven mild asthmatics (Table 2) were recruited for the study in Southampton General Hospital. At the time of enrollment all the asthmatic subjects had stable pulmonary function with a forced expiratory volume in one second ($FEV_1$) greater than 70% of that predicted for their age and height (Table 2). None of the asthmatics were treated with inhaled or oral corticosteroids, sodium cromoglycate or theophylline for at least 6 weeks prior to their participation in this study. They had hyperreactive airways to inhaled methacholine with a geometric mean provocative concentration of agonist required to reduce $FEV_1$ from baseline by 20% ($PC_{20}$) of 1.20 mg/ml (range 0.02–3.25 mg/ml). The asthmatic subjects were all atopic as defined by a >3 mm skin wheal response to one or more of 5 common allergens (*Dermatophagoides pteronyssinus*, mixed grass pollen, dog, feathers and cat dander (Hollister Stier). None of the asthmatics had experienced an upper respiratory tract infection within six weeks of investigations.

Screening.

Subjects attended the laboratory 4 days before the first bronchoscopy when allergen skin prick testing, baseline spirometry and methacholine reactivity testing were performed. The technique used for bronchial challenge was adapted from the 5 breath procedure of Chai et al. (*J. Allergy Clin. Immunol.* 56:323–327, 1975) using an Inspiron nebulizer (CR Bard, Sunderland, U.K.). After recording baseline $FEV_1$, subjects inhaled 5 breaths of 0.9% sodium chloride (saline) from functional capacity to total lung capacity from the nebuliser via a mouthpiece. Measurements of $FEV_1$ were made at 1 and 3 mins and, provided this value did not fall by >10% of baseline, the methacholine provocation was undertaken. Subjects inhaled sequential (doubled) concentrations (0.02–32 mg/ml saline) of methacholine (Sigma Chemical Co.), with $FEV_1$ measurements made 1–3 mins after each inhalation. The stepwise methacholine inhalations continued until the $FEV_1$ had fallen by at least 20% of the post-saline value. The concentration of methacholine was plotted against the percentage fall in $FEV_1$ from post-saline baseline, and that concentration causing a 20% fall in $FEV_1$ ($PC_{20}$) was derived by linear interpolation of the last two data points.

The allergen used for local bronchial challenge (mixed grass pollen or *D. pteronyssinus*) was that which produced the largest wheal response on skin prick testing. In each subject a skin wheal dose response series was then undertaken using 10-fold dilutions of allergen and the concentration chosen for the segmental bronchial challenge was one tenth of the dilution producing a 3 mm wheal response.

Bronchoscopy and Local Challenge.

Study Design.

Volunteers taking part in this study were divided into two groups. A) Normal controls had a single bronchoscopy and BAL and, B) asthmatics had two bronchoscopies 6 hrs apart. Fiberoptic bronchoscopy was undertaken on subjects with $FEV_1$ greater than 70% of predicted, and the platelet and clotting studies were within normal limits. Fiberoptic bronchoscopy was undertaken using a standardized protocol. Subjects received intravenous atropine (0.6 mg and midazolam 3–8 mg) prior to bronchoscopy. Oxygen (100%) was administered via nasal prongs throughout the procedure and oxygen saturation was monitored with a digital oximeter (Minolta, Middlesex, U.K.). Fiberoptic bronchoscopy was performed with Olympus IT-20 bronchoscope (Olympus Optical Co., Tokyo, Japan). Care was taken to ensure that the larynx and upper airways were adequately anesthetised using lignocaine spray (4%). The bronchoscope was passed through the nares and up to 12mls of lignocaine (1%) was introduced through the bronchoscope into the larynx and lower airways. Immediately after this procedure the bronchoscope was wedged into the anterior division of the right upper lobe (RUL) to undertake sham challenge with 20ml of sterile saline solution prewarmed to 37° C. The instrument was then passed into the medial subdivision of the right middle lobe (RML) and 20ml of prewarmed allergen solution was instilled. Five minutes after the introduction of the two solutions, the appearance of the airways was observed and photographed to record airway narrowing. Six hours later a second bronchoscopy was performed with the same premedication and oxygenation. BAL was preformed with 6×20 ml aliquots of prewarmed 0.9% saline solution in both the allergen and saline challenged bronchial segments. Returned fluid was aspirated through the suction channel. Pulmonary function tests ($FEV_1$) were performed 3 hrs after the first bronchoscopy and 3 and 24 hrs after the second.

Lavage fluid processing.

The recovered BAL fluid was centrifuged at 600 g for 15 min at 4° C., the cells separated and the supernatant stored at −70° C. Lavage fluids were concentrated a hundred fold by lyophilization following extensive dialysis, against $ddH_2O$, using Spectapor membranes with a M.W. exclusion point of 3kDa.

Lymphocyte chemotaxis.

Cell migration was performed according to standard methods (Cruikshank et al., *J. Immunol.* 138:3817–3825, 1987). Migration was assessed using a modification of the Boyden chamber assay using a microchemotaxis chamber (Neuroprobe, Cabin John, M. D.). Normal human T lymphocytes were isolated using hypaqueficoll separation of peripheral blood mononuclear cells followed by nylon wool adherence, resulting in >97% $CD3^+$ cells by FACs analysis, and then cultured overnight in RPMI 1640 containing 10% bovine fetal serum. The T cells ($10 \times 10^6$/ml in RPMI 1640) were loaded into the upper well of the chamber, with 30 μl of the BAL fluids placed in the bottom chamber. The two wells were separated by a nitrocellulose filter paper with a pore size of 8 μm. The chamber was incubated at 37° C. for 3hr, after which the filter was stained and migration was assessed by counting the number of cells that had migrated beyond a certain depth into the filter (50μm). For most experiments between 15–20 cells/hpf were counted in the control wells. In inhibition experiments the chemoattractant BAL was mixed with anti-cytokine antibodies (sufficient to neutralize bioactivity of 50 ng/ml of specific protein) for 30min at 37° C. prior to loading the chemotaxis chamber. All migration is expressed as percentage values of cell migration in control buffer.

Antibodies.

A rabbit polyclonal anti-rLCF antibody generated against a rLCF-KLH conjugate purified by protein A sepharose and rLCF affinity chromatography (described herein) was used for ELISAs, western analysis and lymphocyte migration inhibition studies according to standard methods known in the art. Neutralizing anti-MIP1α, RANTES (R&D, Minneapolis, Minn.) and IL-8 (Endogen, Boston, Mass.) antibodies were used according to manufactures specifications. These antibodies were used at concentrations (anti-MIP1α at 20μg/ml, anti-RANTES at 100μg/ml, and anti-IL-8 at 10μg/ml) sufficient to neutralize lymphocyte migration induced by 50 ng/ml of the respective cytokines. There was no detectable cross-neutralization between any of these antibodies for any other cytokine tested.

ELISAs.

ELISAS for LCF were performed using the antibody described above as follows. Recombinant LCF and BAL samples were dissolved in PBS to the appropriate concentrations. Serial dilutions of rLCF were used for the standard curve to which the unknowns were compared. 100 μl of concentrated samples were incubated in duplicate in a 96 well microtitre plate (Nunc) at 37° C. for hr. All subsequent steps were conducted at room temperature. The antigen was removed by washing four times with a PBS-Tween 20 solution. Nonspecific binding was reduced by blocking with 100 μl of 1% BSA for 1hr. Following washing, 100 μl of a rabbit anti-LCF polyclonal antibody (10 μg/ml) diluted in PBS +0.05% Tween 20 was added to each well. The presence of a LCF-anti-LCF complex was detected by the addition of biotinylated goat anti-rabbit IgG (Sigma) diluted 1:500 in PBS, incubated for hr. After washing with PBS, ExtrAvidin peroxidase (Sigma) diluted 1:250 was incubated in each well for 30 mins, the plate was washed and 10μl of freshly prepared substrate was added to the wells. The substrate consists of 0.2mg/ml 2,2'-azino-bis-(3-ethyl-benzthiazoline-6-sulphuric acid) in 0.05M citrate-phosphate buffer, pH 5.3, and 0.015% hydrogen peroxide. The substrate was incubated in the dark for up to 30 min. The results of the ELISA were read at 405 nm with a microplate reader. Using the Softmax program the standard curve of known LCF was established and used to determine the concentrations of LCF in BAL samples.

Quantitation for IL-3, IL-5, MIP1α, RANTES and GM-CSF levels were also assessed in the BAL samples using ELISAs. Commercial ELISA kits and reagents available from Genzyme (Cambridge, MA) for IL-3 and IL-5, Biosource International (Camarilo, Calif.) for GM-CSF, and R & D Systems (Minneapolis, MN) for MIP1α (Endogen, Boston, Mass.) were utilized. All commercial reagents were used according to manufacturers specifications. For all cytokines, control species-specific-antibodies were used to establish background levels. To more accurately quantitate cytokine concentrations, background levels were subtracted from sample measurements.

Results

Lymphocyte Chemotactic Activity From BAL of Normal Individuals.

We first determined whether lymphocyte chemoattractant activity could be identified in the segmental BAL of normal individuals. The demographics of the normal subjects are listed in Table 1.

TABLE 1

Demographics of Normal Subjects

| Subject | Age | Sex | $FEV_{1.0}$ (%)[1] | PC20 (mg/ml)[2] |
|---------|-----|-----|---------------------|------------------|
| N1 | 29 | M | 117.9 | >32 |
| N2 | 25 | M | 114.5 | >32 |
| N3 | 32 | M | 134.2 | >32 |
| N4 | 28 | M | 106.7 | >32 |
| N5 | 60 | F | 113.5 | >32 |
| N6 | 35 | M | 114.0 | >32 |
| N7 | 22 | F | 118.0 | >32 |
| N8 | 20 | M | 104.0 | >32 |
| N9 | 27 | F | 118.5 | >32 |

[1]$FEV_1$ % of predicted based on forced expiratory volume in the 1st second.
[2]Methacholine concentration (mg/ml) required to produce 20% fall in $FEV_1$.

Figure 10:
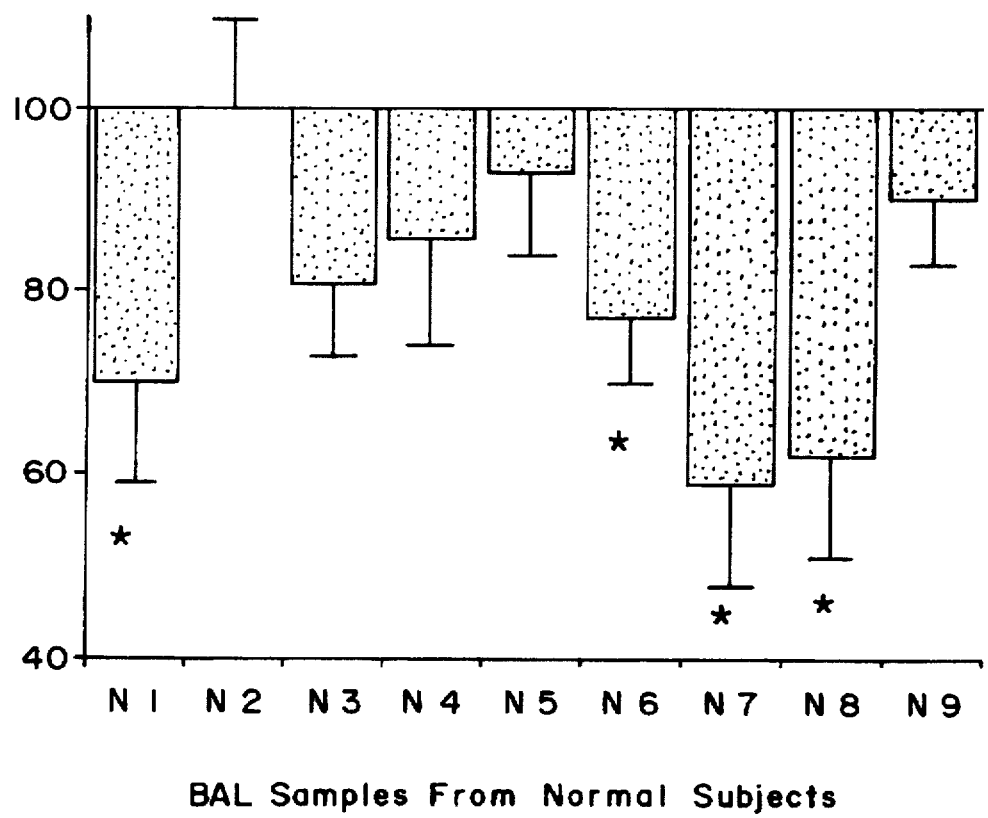

They all were non-atopic and had PC20's to methacholine of greater than 32 mg/ml. We assayed the chemoattractant activity of unconcentrated and one hundred fold concentrated BAL to human peripheral T cells (FIG. 10). Samples were concentrated by first dialyzing against double distilled water followed by lyophilization to effect a 100 fold concentration. Chemotaxis analyses of each undiluted sample did not demonstrate any increase in cell motility as compared with migration in the presence of chemotaxis assay buffer alone. In fact, all of the samples were inhibitory, with significant inhibition of migration (<80% of control migration, p<0.05) detected in 4 of 9 samples. The inhibitory effect did not appear to mask the presence of T cell specific lymphocyte chemoattractant activities of IL-8, RANTES, LCF or MIP1α, in any of the concentrated BAL samples by ELISA (sensitivity >10pg/ml and 40pg/ml respectively). Higher concentrations of normal BAL fluid were more inhibitory; while greater dilutions were less inhibitory, eventually reaching (buffer) control cell migration at a dilution of 1:1,000. For none of the dilutions did BAL fluid from normals induce enhanced migration. In addition there was no detectable lymphocyte chemoattractant activity, for any dilution tested, in BAL six hours following saline challenge of 3 normals who volunteered for dual bronchoscopy studies. These dual BAL samples did demonstrate migration inhibitory activity in a similar fashion as seen with BAL samples obtained from a single lavage from normals.

Lymphocyte Chemoattractant Activity In BAL Fluid Of Asthmatics 6hr Following Antigen Challenge.

Table 2 describes the demographics of the asthmatic subjects.

TABLE 2

Demographics and Characteristics of Asthmatics Subject

| Subject | Age | Sex | $FEV_1$[1] | PC20[2] | Allergen | (mg/ml) |
|---------|-----|-----|------------|---------|----------|---------|
| L1 | 27 | M | 84.1 | 3.45 | grasses | $10^{-4}$ |
| L2 | 42 | F | 105.5 | 3.48 | Derm. Ptery | $10^{-5}$ |
| L3 | 30 | M | 99.3 | 2.99 | grasses | $10^{-5}$ |
| L4 | 33 | F | 104.0 | 1.47 | Derm. Ptery | $10^{-5}$ |
| L5 | 25 | M | 76.2 | 2.28 | Derm. Ptery | $10^{-5}$ |
| L6 | 37 | F | 88.9 | 2.96 | grasses | $10^{-5}$ |
| L7 | 28 | M | 90.0 | 1.70 | grasses | $10^{-5}$ |

[1]$FEV_1$ % of predicted based on forced expiratory volume in the 1st second.
[2]Methacholine concentration (mg/ml) required to produce 20% fall in $FEV_1$.

Figure 11:
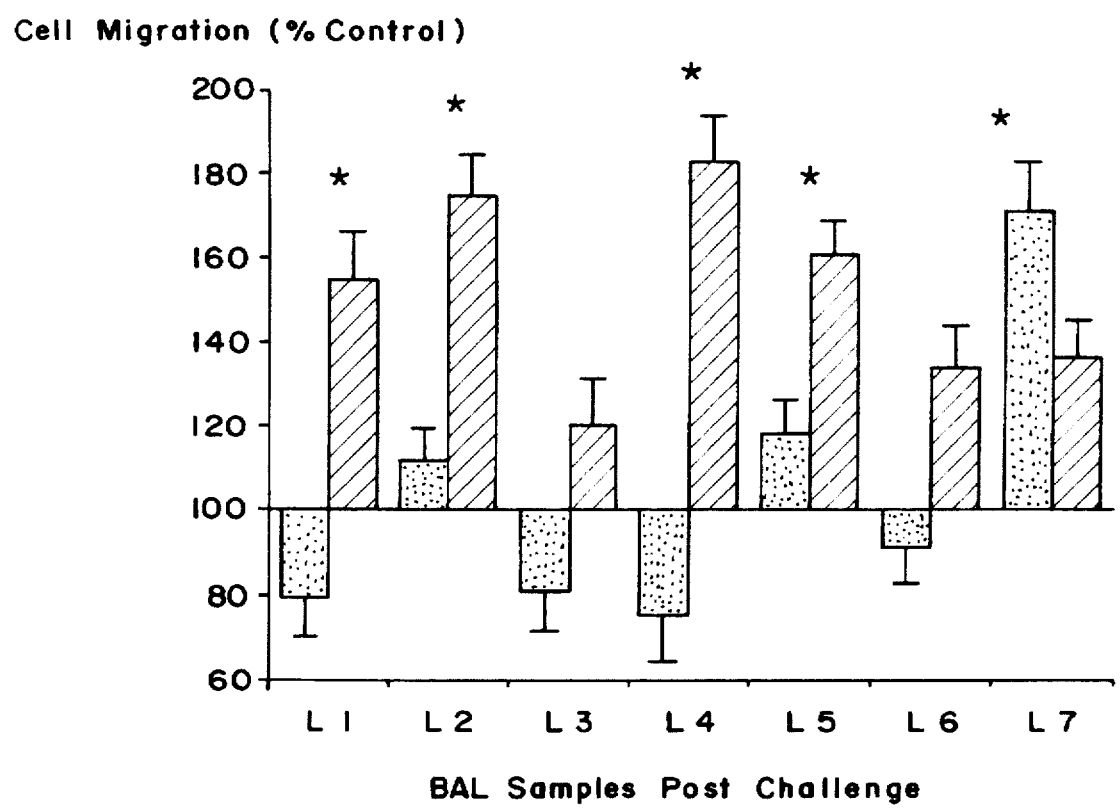

FIG. 2 depicts the lymphocyte chemoattractant data from the BAL fluid of asthmatics challenged with antigen as described above. While the BAL fluid from normals demonstrated predominantly inhibitory activity, following saline challenge of asthmatics (FIG. 11) the subsequent concentrated saline BAL were less inhibitory and, in some samples, chemoattractant activity was detected. Specifically, in individuals L1, L3, L4 and L6 the BAL following saline challenge reduced migration to below control, appearing like the BAL of normal individuals. The BAL fluid of the saline challenged lobes of individuals, L2 and L5, and L7 had some baseline lymphocyte chemoattractant activity; L7's BAL fluid contained significant T cell chemoattractant activity. However, we did detect an increase in lymphocyte chemoattractant activity in the antigen challenged, unconcentrated, subsegmental BAL from six of the seven asthmatics (FIG. 11) compared to their saline challenged lobes (p<0.05for each except L7). Four of the seven antigen samples (L1, L2, L4, and L5) demonstrated significant increases in migration compared to control migration buffer. BAL samples L3b and L6b did induce significant increased migratory responses compared to their saline control (p<.05) but compared to chemotaxis buffer, the levels did not reach statistical significance (p>0.05). None of the saline or antigen challenge solutions had any intrinsic lymphocyte chemoattractant activity.

As shown in Table 3, there were no detectable changes in cell differentials following antigen challenge. On average the recovered cell population in the BAL fluid remained consistent pre- and post-antigen challenge with cell differentials of 65–70% macrophages, 13–20% lymphocytes, 17–21% neutrophils, and 4–10% eosinophils. This finding suggests that the cytokines present in the BAL fluid at the 6 hr time point were produced by either pre-existing or newly recruited cells at the site of antigen challenge. This also indicates that chemoattractants detected at this early time point play a role in recruitment of responding cells.

TABLE 3

Differential Cell Counts 6 hrs Post Saline or Allergen Challenge[1]

| Subjects | Macro-phage | Lympho-cyte | Neutro-phil | Eosinophil | Cells Counted | Total Cells/ml |
|----------|-------------|-------------|-------------|------------|---------------|----------------|
| L1a[2] | 522 | 108 | 139 | 31 | 800 | $9.6 \times 10^4$ |
| L1b[3] | 539 | 126 | 93 | 45 | 803 | $9.6 \times 10^4$ |
| L2a | 557 | 195 | 48 | 5 | 805 | $6.8 \times 10^4$ |
| L2b | 271 | 85 | 403 | 46 | 805 | $8.2 \times 10^4$ |
| L3a | 515 | 237 | 47 | 2 | 801 | $6.8 \times 10^4$ |
| L3b | 453 | 162 | 195 | 4 | 814 | $4.0 \times 10^4$ |
| L4a | 457 | 284 | 59 | 5 | 805 | $13.9 \times 10^4$ |
| L4b | 384 | 289 | 118 | 13 | 804 | $25.9 \times 10^4$ |
| L5a | 411 | 226 | 167 | 1 | 805 | $8.8 \times 10^4$ |
| L5b | 552 | 118 | 84 | 52 | 806 | $7.9 \times 10^4$ |
| L6a | 750 | 25 | 22 | 7 | 804 | $2.0 \times 10^4$ |
| L6b | 640 | 23 | 137 | 10 | 810 | $3.3 \times 10^4$ |
| L7a | 291 | 236 | 270 | 22 | 819 | $11.3 \times 10^4$ |
| L7b | 460 | 173 | 105 | 65 | 803 | $8.6 \times 10^4$ |

[1]Cell counts were performed on recovered BAL fluid from an instillation volume of 120 ml. Following centrifugation, cell pellets were cytospin centrifuged and stained with a Wright's-Giemsa's stain.
[2]Cells obtained 6 hrs following saline challenge are designated by an "a".
[3]Cells obtained 6 hrs following antigen challenge are designated by a "b".

Characterization Of The Lymphocyte Chemoattractant Activity.

Figure 12A:
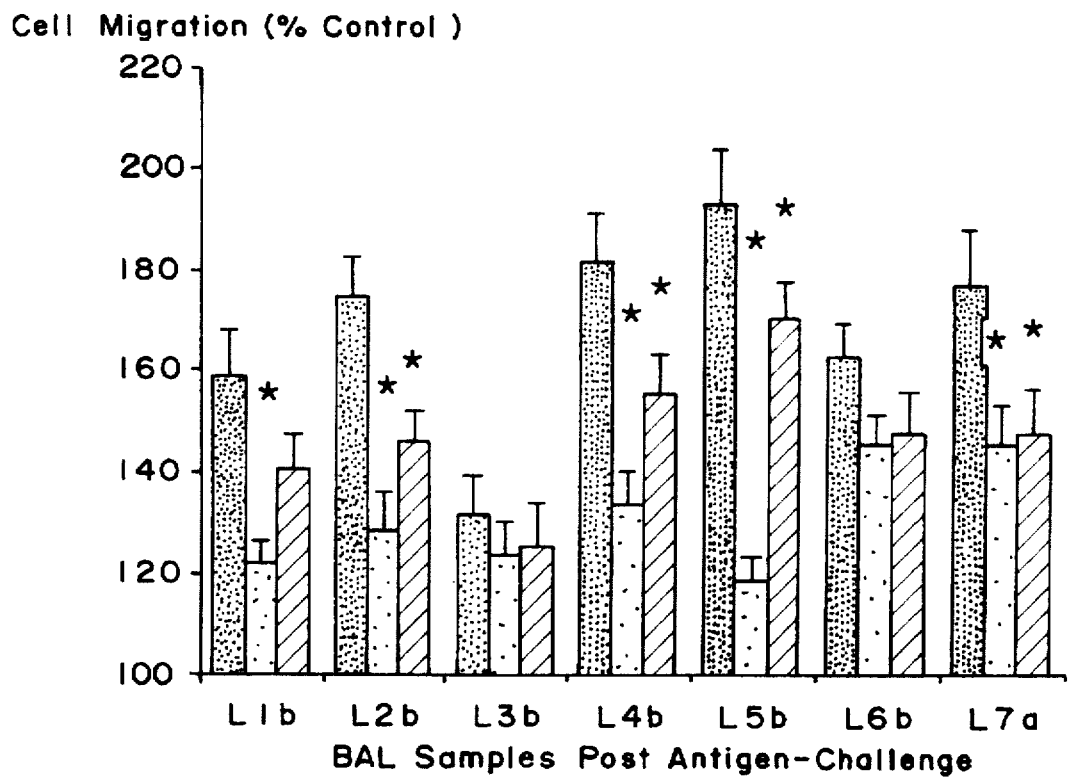
Figure 12B:
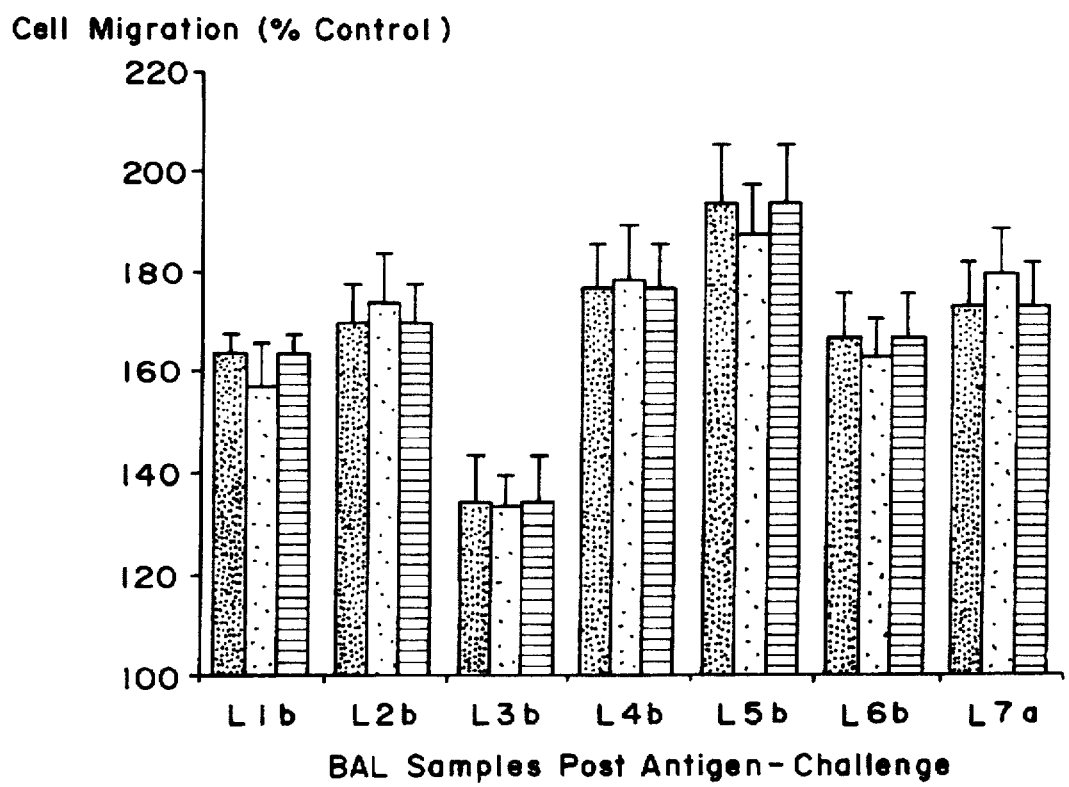
Figure 13:
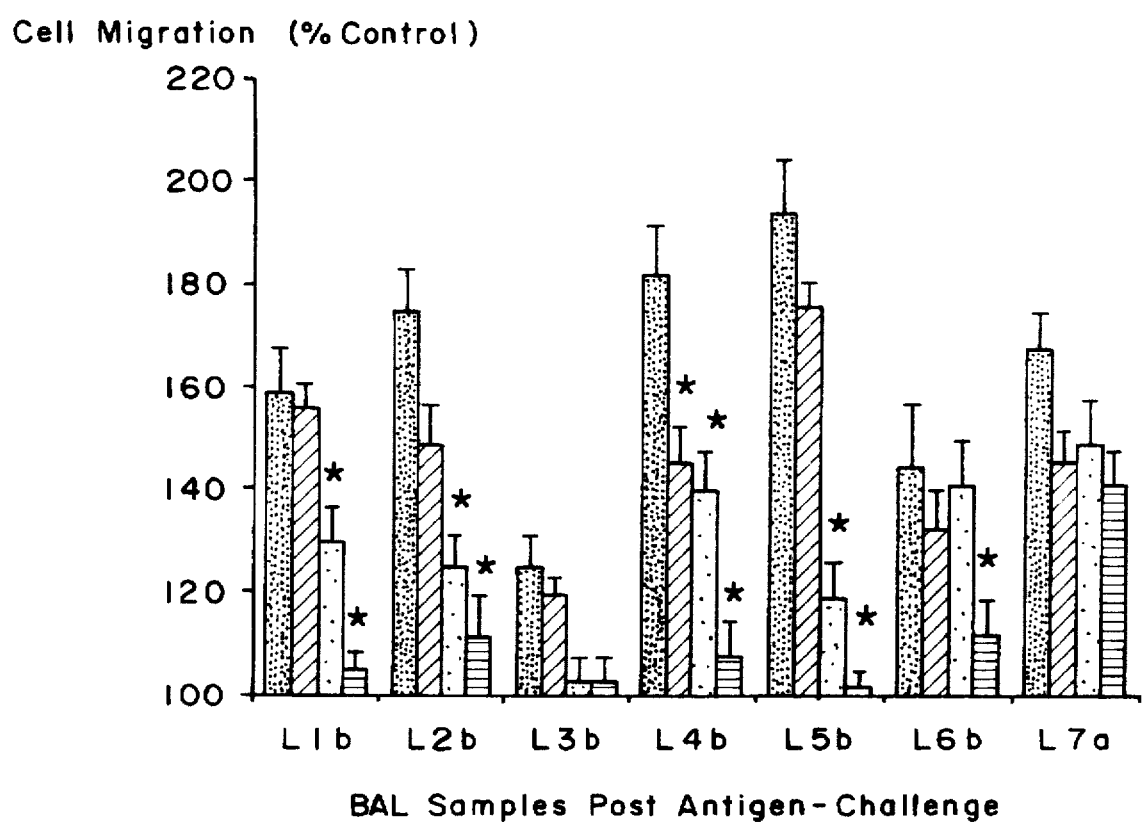

Initial characterization of the chemoattractant activity from the BAL of antigen challenged lobes was conducted using neutralizing antibodies to known lymphocyte chemoattractants. Neutralizing antibodies to LCF, IL-8, MIP1α, and RANTES were used in this study. Co-incubation of the BAL samples with 1 µg/ml anti-LCF polyclonal antibody (sufficient to neutralize 50 ng/ml of LCF bioactivity) for 30min prior to the chemotaxis assay, reduced the chemoattractant activity for each of the samples (FIG. 12). However, anti-LCF antibody did not completely inhibit the migratory response to any of the BAL samples, as compared with the saline control values, indicating that other chemoattractants were also present. Co-incubation with neutralizing antibodies for IL-8 or RANTES bioactivity had no effect on the lymphocyte chemoattractant activity, while antibodies to MIP1α did have an inhibitory effect. (FIG. 12). Samples L2b and L4b demonstrated the greatest percent blocking by anti-MIP1α alone. A combination of anti-LCF and anti-MIP1α inhibited 90–95% of all induced migration of each of the BAL's following antigen challenge (FIG. 13). The addition of the other antibodies to either anti-LCF or anti-MIP1α did not further reduce the migratory response. Interestingly, individual L7 had demonstrated significant chemoattractant activity following saline challenge. When this sample was co-incubated with anti-LCF or anti-MIP1α antibodies, the migratory response was partially reduced (FIG. 12). A combination of anti-LCF and anti-MIP1α did not completely eliminate all induced migration (FIG. 13) indicating that other chemoattractants are present. Overall, the major lymphocyte chemoattractant activity was LCF in the antigen challenged BAL. In total, approximately 90–95% of all the chemoattractant activity was attributed to a combination of LCF and MIP1α.

Detection Of LCF And MIP1α Protein By ELISA.

We next determined whether these same samples had detectable levels of LCF and MIP1α protein. Table 4 shows the results of these ELISAs of the BAL from antigen and saline challenged lobes expressed as pg/ml of total BAL volume. The LCF concentrations were determined from concentrated BAL corrected to starting volume.

TABLE 4

ELISA-quantitated LCF and MIP1α Concentration in BAL[1] in asthmatic subjects

| Subjects | LCF (pg/ml) | | MIP1α (pg/ml) | |
| --- | --- | --- | --- | --- |
| | Saline | Antigen | Saline | Antigen |
| L1 | <10 | 1003 | <40 | <40 |
| L2 | <10 | 7042 | <40 | 503 |
| L3 | <10 | <10 | <40 | 75 |
| L4 | <10 | 11035 | <40 | 720 |
| L5 | <10 | 9052 | <40 | 95 |
| L6 | <10 | 958 | <40 | 88 |
| L7 | 208 | 64 | 55 | 73 |

[1]BAL samples were concentrated from 50 ml to 0.5 ml by spin centrifugation. The ELISA for LCF was conducted using a protein A purified rabbit anti-rLCF antibody, and detected by a biotin-conjugated goat anti-rabbit polyclonal antibody. The sensitivity for the assay ranged from 10 pg/ml to 20 ng/ml. The MIP1α ELISA, available from R and D Systems, was conducted using the manufacturers specifications. The sensitivity of the assay ranged from 40 pg/ml to 2 ng/ml. Each sample was run in triplicate and the data represents the average of the three values.

One hundred microliters of each BAL sample was assayed concentrated 100 fold from the original volume of lavage fluid. The data are expressed as pg/ml of BAL sample corrected to the orginal BAL volume. Allergen challenged asthmatic BAL L2b, L4b and L5b had values close to 1 ng/ml. For L2b this was an LCF protein concentration of 47 ng/ug of total protein (total protein assessed by Bradford Protein Analysis), for L5b, 13.5 ng/ug total BAL protein and 1.5 ng/ml for sample L4b which was 89 ng/ug unconcentrated BAL protein. We did not detect any LCF from concentrated BAL of saline challenged lobes, and subjects 3, and 6 had undetectable LCF by ELISA in their antigen challenged lobes. This is consistent with the relative amount of LCF-induced bioactivity observed for these samples and the greater sensitivity of the chemotaxis assay as compared with the ELISA.

Detectable levels of RANTES were not observed at the 6hr time point following either saline or antigen challenge in the BAL fluid. These data combined with the lack of neutralizing effects by the anti-RANTES antibodies indicates that RANTES were not present at the 4–6hr time point.

The quantitation of MIP1α protein by ELISA is also shown in Table 3. The two BAL samples which demonstrated the largest percent blocking by anti-MIP1α antibodies, L2b and L4b, exhibited MIP1αprotein in the range of 600pg/ml (corrected to original BAL volume) (Table 3). Several other samples, L3b, L5b, and L7b, had trace amounts of detectable MIP1α protein. For both chemoattractants the samples which displayed the greatest chemoattractant activity also demonstrated the highest detectable levels of protein. At this six hour time point following antigen challenge there were no measureable levels of cytokines IL-3, IL-5 or GM-CSF by ELISA, with a lower sensitivity limit of 40pg/ml, in aliquots of the same BAL samples. Detectable levels of IL-8 protein were present in all antigen challenge and most saline challenged lobes.

Stimulation of Cell Division Using LCF and A Growth Factor

We have discovered that recombinant LCF induces the expression of cell receptors, e.g., IL-2R, which subsequently render a cell-bearing the receptor, e.g., a T cell, competent to respond to its cognate growth factor, e.g., IL-2. In one working example, human T cells were stimulated with recombinant LCF (a concentration range of $10^{-5}$M to $10^{-10}$M was used with similar results, data for $10^{-8}$M is shown) for 24h at which time rIL-2 (2U/ml) or anti-CD3 (OKT3, 50 ng/ml) were added to the cell cultures. Four days after the addition of either rIL-2 or OKT3 antibody cell proliferation was assayed by $^3$H thymidine uptake. Averaging the results of all three experiments shown in Table 5, showing the effects of recombinant LCF on anti-CD3 and rIL-2 induced thymidine incorporation, recombinant LCF preincubation resulted in enhanced IL-2 responsiveness. Human T cells do not increase the incorporation of $^3$H thymidine following incubation with recombinant LCF alone at either 24 or 48h, but following preincubation with recombinant LCF, rIL-2 stimulated T cells increase their incorporation of $^3$H thymidine from 1.079 cpm to 13.818 cpm. However, in the recombinant LCF treated Cell cultures the proliferative response to anti-CD3 antibody was reduced approximately 50% from 21,257 cpm for anti-CD3 stimulation alone to 12,047 cpm in cell stimulated with recombinant LCF.

Thus, in the example given human T cells were incubated with recombinant LCF for 24 hours prior to stimulation with the T cell growth factor interleukin 2. Prior incubation of T cells with recombinant LCF resulted in a 5 fold increase in incorporation of $^3$H-thymidine (DNA synthesis) at 72 hours compared to either recombinant LCF or rIL-2 alone. This synergy was specific for IL-2 as prior incubation of T cells with recombinant LCF decreased subsequent $^3$H-thymidine incorporation in response to T cell antigens (see anti-$CD_3$ responses).

TABLE 5

| Stimulus | Expt. 1 | Expt. 2 | Expt. 3 |
| --- | --- | --- | --- |
| Control | 983 ± 145 | 1074 ± 326 | 946 ± 197 |
| LCF ($10^{-8}$M) | 1203 ± 284 | 1054 ± 212 | 982 ± 301 |
| Anti-CD3 (50 ng/ml) | 22485 ± 1077 | 20496 ± 998 | 20792 ± 1048 |
| rIL-2 (IU/ml) | 2381 ± 185 | 2594 ± 464 | 2508 ± 4071 |
| LCF + anti-CD3* | 12497 ± 1038 | 11739 ± 335 | 11905 ± 1127 |
| LCF + rIL-2* | 12664 ± 2802 | 15037 ± 1088 | 13753 ± 2068 |

*Cultures were stimulated with LCF for 24 hr prior to the addition of either anti-CD3 antibody or rIL-2. Cultures were conducted for a total of 5 days.

Next, we evaluated the effect of media, rIL-2, rLCF, and rLCF on human nylon wool non-adherent T cells (NWNAT)

Figure 14:
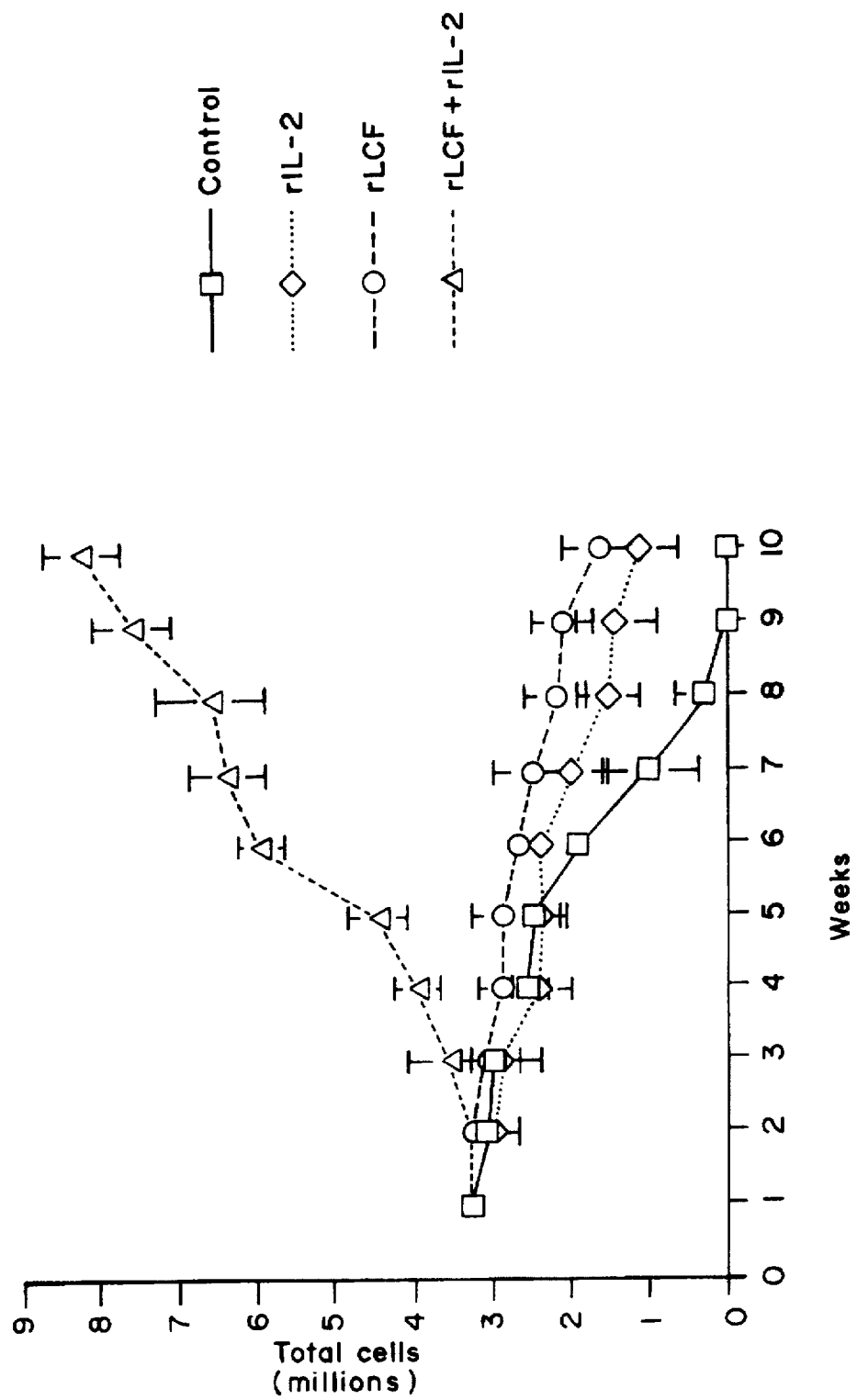
FIG. 14 shows the effect of media, rIL-2, rLCF, and rLCF and IL-2 on human nylon wool non-adherent T cells (NWNAT) proliferation.

(Julius et al., Eur. J. Immunol. 3:645, 1973) proliferation under long term culture conditions. The results of eight individual experiments (performed in duplicate) are shown in FIG. 14. Cells were plated at $3 \times 10^6$/ml in one ml cultures. In the rLCF culture and the rIL-2culture, the cytokines were added every two days. The dosing schedule for rLCF/rIL2 was rLCF ($10^{-10}$M) each Monday, followed every Wednesday and Friday by rIL-2 (10U/ml). Cell counts were performed once every week.

The mean total of numbers of cells present in the one ml cultures are depicted on the ordinate of FIG. 14. In the cultures containing only media and cultures treated with rIL-2 alone, cell numbers declined by half. Treatment with rLCF preserved cell numbers, while treatment with rLCF and rIL-2 increased cell numbers to over twice the original plating density, resulting in nearly four times greater mean cell numbers found in cultures treated with rIL-2 or untreated cells at six weeks.

Figure 15:
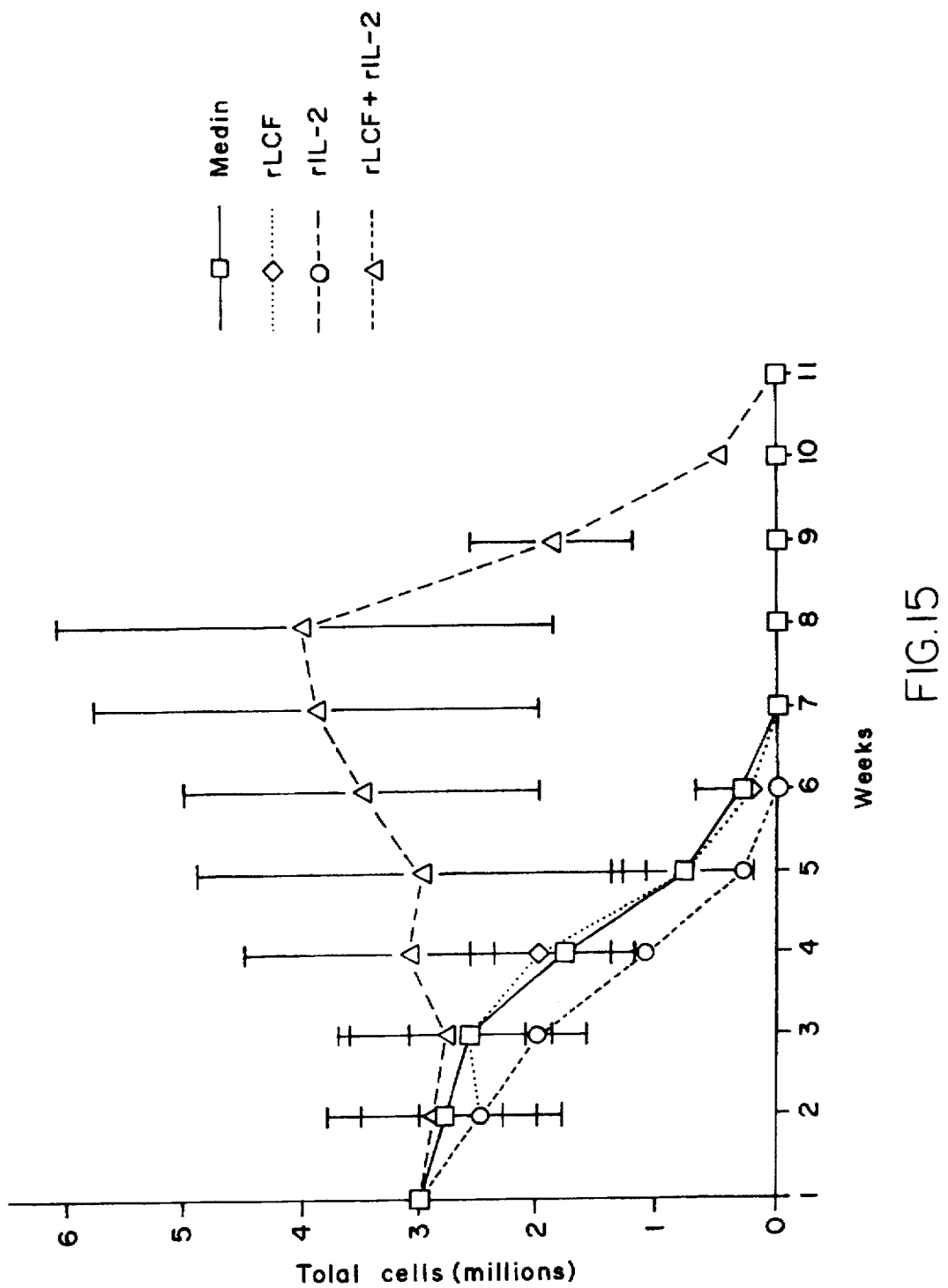
FIG. 15 shows the effect of media, rIL-2, rLCF, and rLCF and IL-2 on human HIV+PMBCs.

We next examined the effect of the above treatments using long term HIV+PBMCs. The growth kinetics of long term PMBC cultures obtained from five HIV+individuals are shown in FIG. 15. Using the culture conditions described above, we examined the effect of rLCF, rIL-2, rLCF followed by addition of rIL-2, or media alone on the viability and proliferation of HIV+PBMCs. Cultures were plated at $3 \times 10^6$ per ml and maintained in one ml cultures with the addition of cytokines as outline above. The results shown in FIG. 15 demonstrate that PBMCs of HIV+patients in unstimulated culture, IL-2 treated, or rLCF treated cultures undergo rapid early cell depletion and by 6–7 weeks more than 90% of the cells have lysed. Compared to untreated cells, IL-2 at 10U/ml did not lead to a proliferative response. In addition, rLCF did not increase cell survival nor increase the rate of cell lysis when compared to control or IL-2 treatments. The results also show that cells cultured with rLCF($10^{-10}$M) in combination with IL-2(10U/ml) not only survive, but proliferate for at least 9 weeks. The difference in cell survival between combined rLCF and rIL-2 and control, using paired t-test analysis, is statistically significant at p=0.02. All of these surviving and proliferating cells were CD4+.

Figure 16:
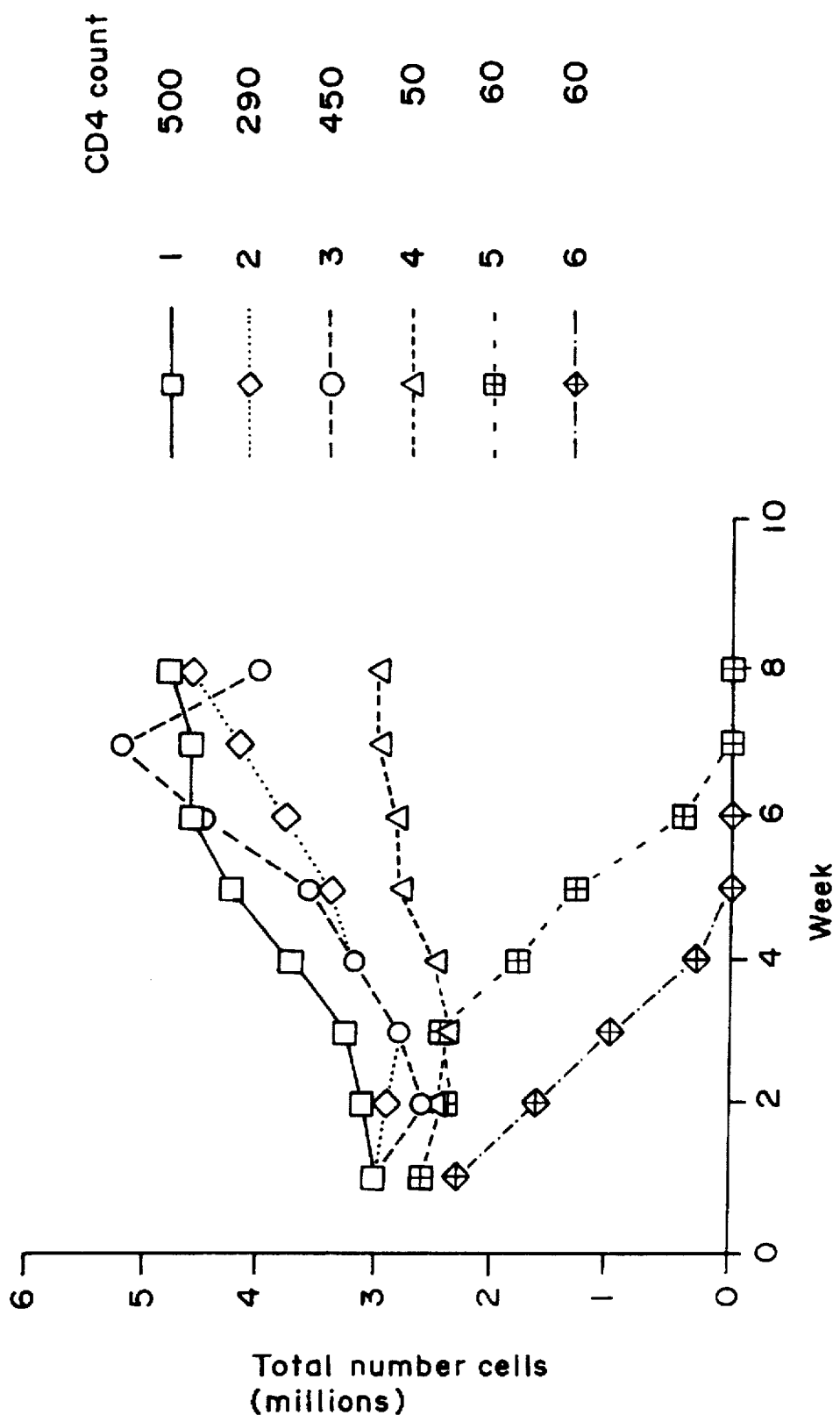
FIG. 16 shows the cell counts of long term cultures of rLCF and rIL-2 treatments with CD4 counts obtained from patients infected with HIV. Data for 5 and 6 represent the same individual a month apart.

These data were then evaluated in the context of the patient's CD4 count shown in FIG. 16. The data shown in FIG. 16 demonstrate that the proliferative response of HIV+ PBMCs due to rLCF and IL-2 treatment is greater in those patients having CD4 counts over 50. The results also appear to suggest that the cultures have a lower chance of survival when the CD4 count is low. (The two curves where the cultures did not survive (Data for curves 5 and 6) belong to the same patient, and that the CD4 count had not changed during the month interval between the experiments.) As shown in FIG. 16, all the patients have CD4 counts of less than or equal to 500. Of these, ¾ of the patients that had the greater proliferative response had a CD4 count of >290. The CD4/CD8 ratio for all the individuals ranged between 0.1 and 0.4. Furthermore, three patients with the highest proliferative response, also had the highest ratios, 0.3 and 0.4.

Figure 17:
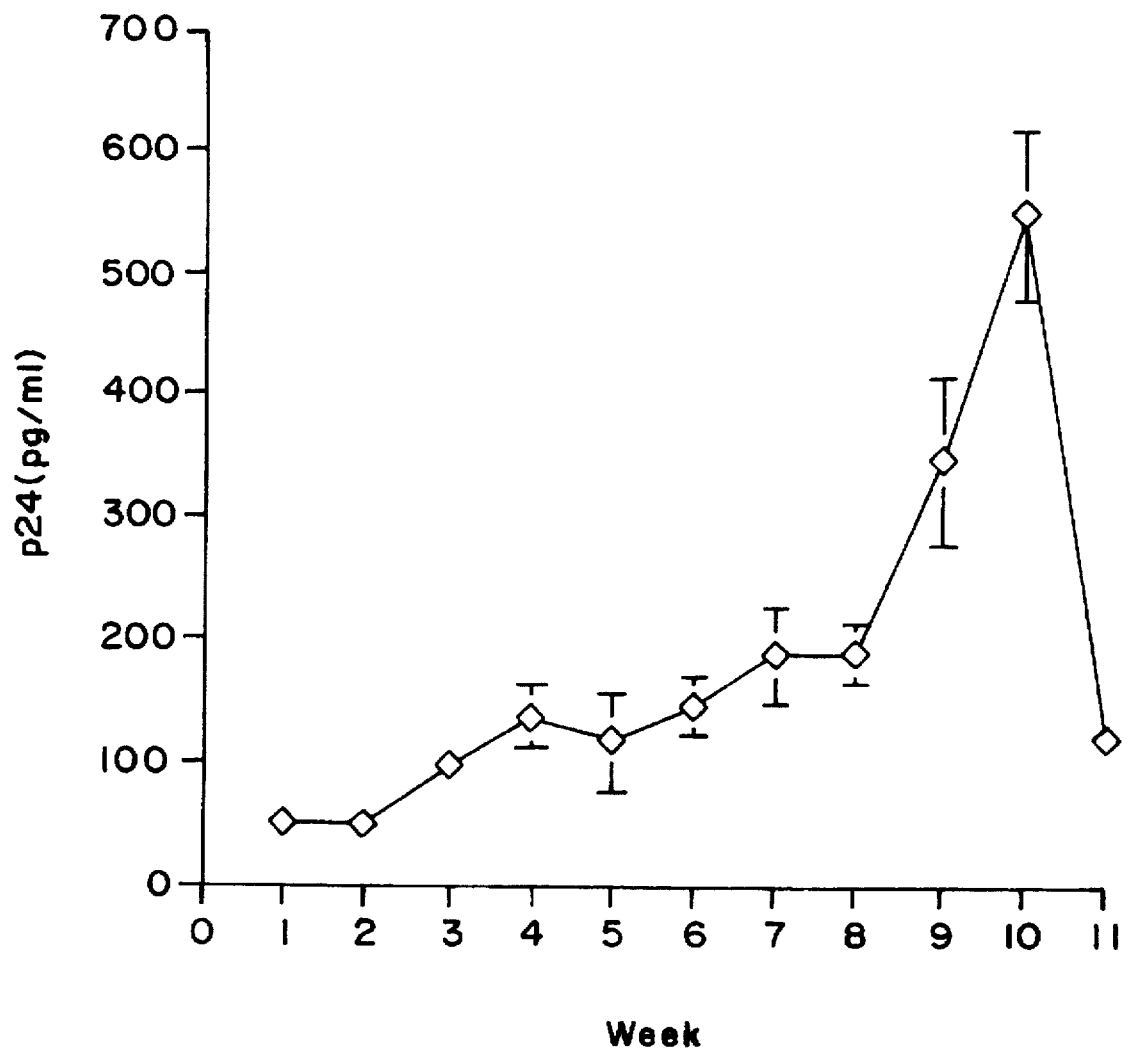
FIG. 17 shows p24 measurement by ELISA.

The loss of cells beyond week 9 suggests that HIV infection has an adverse effect on these cultures. To further investigate this decline in cells, we performed p24 ELISA measurements on the cultures according to methods known in the art. As shown in FIG. 17, there is a four-fold increase in the p24 measurements, indicating that while cells are activated and induced to proliferate, the virus is also proliferating. Accordingly, it is possible that by week 9 viral replication leads to cell lysis. Given this result, an antiretroviral agent, e.g., AZT or ddI, should be included in the culture to reduce viral load.

These results demonstrate that there is both survival and proliferation of HIV+PBMCs cultures when treated with rLCF and rIL-2. Based on our discovery (described above) that rLCF preserves CD4+ T cell numbers and in combination with rIL-2 increases CD+4 T cells, therapies, in vivo or ex vivo or both, are made available for reconstituting the immune system, e.g., by preserving, increasing, and/or expanding the number of CD4+ cells, as described herein.

In one working example, evaluation of whether ex vivo and in vivo treatment using rLCF in combination with a growth factor, e.g., rIL-2, confers protection against the development of an immune disorder, e.g., AIDS, generally involves using standard animal models (e.g., Hu-PBL-SCID or the Hu-PBL-SCID-HIV mouse models). For evaluation of in vivo therapy, an appropriate animal is treated with rLCF and a growth factor, e.g., rIL-2, and if desired, an antiretroviral agent such as AZT or ddI, according to any standard method, and a reduced incidence of the development of an immune disorder, e.g., AIDS, compared to untreated control animals, is detected as an indication of protection. In general, the scheduling for administering rLCF and a growth factor follows the scheduling of adding rLCF and rIL-2 to cell cultures described above. This protocol is then repeated, as necessary. Alternatively, rLCF and a growth factor are administered simultaneously. Recombinant compositions and antiviral agents are administered according to methods known in the art, e.g., by intravenous or subcutaneous injection, in pharmaceutically-acceptable formulations. Optimization of the dosing parameters and scheduling the administration of the LCF and the growth factor is carried out according to methods known in the art.

Alternatively, for evaluation of ex vivo therapy, PMBCs are collected from an appropriate animal on the day the blood is drawn according to standard techniques. For example, blood samples are diluted in equal volume phosphate-buffered saline and layered over a ficoll/hypaque density gradient. After centrifugation, the PMBC suspension is aspirated from the interface. Collected PMBCs are washed in PBS and viability and cell numbers are determined by microscopy according to standard techniques, e.g., using trypan blue and Turk's crystal violet stains. PMBC suspensions are brought to volume in PBS to be used for reconstitution of an appropriate animal model, e.g., SCID, and treated with rLCF and a growth factor, and, if desired, an antiviral agent, as described above. Treatment of the cell cultures is continued, e.g., for 8–12 weeks, after which time the cells are reintroduced to the donor animal. If necessary the process is repeated. Alternatively, the rLCF and growth factor are administered simultaneously. Animals receiving ex vivo treatments having a reduced incidence of the development of an immune disorder, e.g., AIDS, compared to untreated control animals, are an indication of protection. Optimization of the dosing parameters and scheduling the administration of the LCF and the growth factor is carried out according to methods known in the art.

LCF Anatagonists As Anti-Cancer Agents

Anti-cancer agents of the invention, e.g., LCF antagonists (as described above, for example, a fragment or analog of LCF, or an anti-LCF antibody) are useful for inhibiting a neoplasm, e.g., CD4+ leukemias or lymphomas, or any malignant cell bearing CD4+ receptors. Those skilled in the art will understand that any number of methods, both in vitro and in vivo, are used to determine the efficacy of anti-cancer agents useful in the methods of the invention. For example, the reduction of neoplasmic growth can be monitored in a mouse or rat growing a cancer following the administration of the test compound. In a working example, a neoplasmic cell line growing in culture (e.g., those cell lines described herein) is released from monolayer by trypsinization, diluted into single-cell suspension and then solidified by centrifugation into a pellet which is subsequently exposed to 15 μl fibrinogen (50 mg/ml) and 10 μl thrombin (50 units/ml) for 30 minutes at 37° C. Fibrin clots containing tumor are then cut into pieces approximately 1.5 mm in diameter. Each piece of tumor is subsequently implanted under the kidney capsule of a mouse according to standard methods. Generally, administration of the test molecule is initiated prior to neoplasmic implantation and/or after neoplasmic implantation. Control animals receive a placebo, e.g., serum albumin or diluent, similarly administered as for the LCF inhibitor or related molecules. The effect of the test molecule on neoplasmic growth is monitored according to any standard method. A molecule shown experimentally to halt or reduce or inhibit the growth of such an implanted neoplasm is considered useful in the invention.

Evaluation of whether a test compound confers protection against the development of a neoplasm (e.g., CD4+ leukemias or lymphomas) also involves using an animal known to develop a neoplasm (e.g., the transgenic mouse described in U.S. Pat. No. 4,736,866). An appropriate animal is treated with the test compound according to standard methods, and a reduced incidence of neoplasm development, compared to untreated control animals, is detected as an indication of protection.

Alternatively, the evaluation of whether a test compound confers protection against the development of a neoplasm is evaluated in vitro according to any standard method known in the art. Cell lines useful for examining the in vitro effects of a LCF inhibitor include, without limitation, SUP-T1 (ATCC CRL 1942); J45.01 (ATCC CRL 1990); J-111 (ATCC CRL 8129); J-A1886 (ATCC CRL 8130); 8E5 (ATCC CRL 8993); C5/MJ (ATCC CRL 8293; D10.G4.1 (ATCC TIB 224); HVS-SILVA 40 (ATCC CRL 1773); CTLL-2 (ATCC TIB 214); HuT 102 (ATCC TIB 162); Mo (ATCC CRL 8066); Mo-B (ATCC CCL 245); HUT 78 (ATCC TIB 161); and THP 1 (ATCC TIB 202). A molecule shown experimentally to halt or reduce or inhibit the growth of such cell lines is considered useful in the invention.

As is discussed below, we have discovered that an LCF inhibitor has been found to be a potent inhibitor of neoplasmic THP1 growth in vitro. The experimental example described below demonstrates the efficacy of anti-LCF antibodies as an anti-cancer agent. This example is provided to illustrate, not limit, the invention.

Our finding that LCF demonstrates a CD4 dependent transition from $G_o$ to $G_1$ (marked by the induction of IL-2R and HLA-DR) prompted us to pursue the possibility that this response might be TcR/CD3 independent. The chemotactic response of TcR(−) monocytes and eosinophils further suggested that the presence of CD3 is not an absolute requirement for CD4 signaling. In order to pursue this hypothesis we utilized a CD4+CD8+CD3− T cell line Sup-T1, which we found to exhibit a motile response to LCF and Leu3a antibodies. In addition, we found that the LCF induced response is inhibited by both anti-LCF antibodies and rsCD4.

To determine if Sup-T1 was a suitable cell line to dissect the differences between motility and growth signals we investigated the effects of LCF and LCF inhibition on SupT1 cell growth. This experiment was carried out as follows. Sup T1 cells were cultured in the presence or absence of LCF for 24 hrs according to standard methods, after which time the cells were loaded with the metachromatic dye, acridine orange, for determination of DNA and RNA content. The results showed that there is a marked cell cycle change with many cells progressing into S, $G_2$ and M. This finding is in contrast to normal T cells which progress only as far as $G_1$ following stimulation with LCF. In addition, we also examined the ability of Sup-T1 to take up $^3$H thymidine. For these experiments, $5 \times 10^5$ cells per well were cultured for 24hrs with or without the addition of either rLCF or monoclonal anti-LCF antibody. The wells were pulsed for 8 hrs with 1 μCi $^3$H-thymidine and quantitated by scintillation counting. Data obtained from these experiments are shown in Table 6 (the average of three sets of experiments each performed in triplicate). In addition, Northern analysis failed to detect any message for either IL-2, IL-4 or IL-2R. Accordingly, the growth of Sup T1 is IL-2 and IL-4 independent, but it can be altered by LCF interaction with CD4.

TABLE 6

| | Effects of rLCF and Anti-LCF Antibody on Supt1 and THP1 Growth | | |
|---|---|---|---|
| Cells | Alone | +anti-LCF (10 ug/ml) | +LCF ($10^{-8}$M) |
| SUPT1 | 37,835 +/− 968 | 39,804 +/− 1175 | 59,804 +/− 1175 |
| THP1 | 21,847 +/− 1137 | 10,592 +/− 1091 | 29,478 +/− 1284 |

Experiments investigating the effects of LCF and anti-LCF antibodies on growth of the CD4+ receptor bearing cell line are shown in Table 6. We found that additional exogenous LCF increased $^3$H thymidine incorporation. Moreover, THP1 cells cultured in the presence of anti-LCF antibody alone decreased the normal $^3$H thymidine incorporation of these cells by at least 50% (Table 6). This response is IL-2R/IL-2 independent as anti-IL-2 and anti-Tac have no effect on the LCF-CD4 related cell cycle changes.

As demonstrated above, anti-LCF antibodies are effective in inhibiting neoplasmic growth of CD4+ cells, e.g., THP1, and SUP-T1. Accordingly, compounds of the invention can be formulated according to known methods to prepare pharmaceutically useful compositions as described herein. Treatment of human patients will be carried out using a therapeutically effective amount of an anti-cancer agent of an LCF inhibitor in a physiologically acceptable carrier. Suitable carriers and their formulation are described for example in Remington's *Pharmaceutical Sciences* by E. W. Martin. The amount of the anti-cancer agent to be administered varies depending upon the manner of administration, the age and body weight of the patient, and with the type of disease, extensiveness of the disease, and size of the patient suffering from the disease. Generally amounts will be in the range of those used for other agents used in the treatment of cancer, although in certain instances lower amounts will be needed because of the increased specificity of the compound. For example, an anti-LCF antibody is administered systemically, as described below, at a dosage that inhibits malignant cell proliferation, typically in the range of 0.1 ng–10 g/kg body weight.

Furthermore, the method of the invention can also employ combination therapy in which an LCF inhibitor is administered either simultaneously or sequentially with a chemotherapeutic agent. Typically, a chemotherapeutic agent is administered according to standard methods or,alternatively, in a dose which is lower than the standard dose when the chemotherapeutic agent is used by itself. Examples of chemotherapeutic agents include, without limitation, mechlorethamine, cyclophosphamide, ifosfamide, L-sarcolysin, chlorambucil, hexamethylmelamine, thiotepa, busulfan, carmustine, lomustine, semustine, streptozocin, dacarbazine, methotrexate, fluorouracil, cytarabine, mercaptopurine, thioguanine, pentostatin, vinblastine, vincristine, etoposide, teniposide, actinomycin D, daunomycin, doxorubicin, bleomycin, plicamycin, mitomycin, cisplatin, mitoxantrone, hydroxyurea, procarbozine, mitotane, aminoglutethimide, prednisone, hydroxyprogesterone, diethylstilbestrol, tamoxifen, flutamide, or leuprolide. Treatment is started generally with the diagnosis or suspicion of a neoplasm and is generally repeated on a daily basis. Protection from the development of a neoplasm is also achieved by administration of an LCF inhibitor on a daily basis. If desired, the efficacy of the treatment or protection regimens is assessed with the methods of monitoring or diagnosing patients for cancer. Furthermore, the anti-cancer compounds of the invention can also be used to treat mammals to destroy any unwanted cells bearing CD4+ receptors associated with a pathological condition.

LCF Kits

Kits for carrying out the above methods and using the above compositions are also included in the invention. Such kits preferably include a substantially pure antibody that specifically recognizes and binds a LCF polypeptide, and may also include means for detecting and quantitating antibody binding. Alternatively, the kit may include all or a fragment of a LCF nucleic acid sequence useful for hybridization purposes, and may also include means for detecting and quantitating LCF RNA hybridization.

Therapy

Particularly suitable therapeutics for the treatment of hyperresponsive immune responses and inflammatory diseases are the soluble antagonistic fragments described above formulated in an appropriate buffer such as physiological saline. Furthermore, anti-LCF polypeptide (fragments or analogs thereof) antibodies produced as described above may be used as therapeutics. Again, the antibodies would be administered in a pharmaceutically-acceptable buffer (e.g., physiological saline). If appropriate, the antibody preparation may be combined with a suitable adjuvant. Similarly, the methods of the invention provide for the identification of an organic compound useful to antagonize LC4:CD4 interaction, once identified and isolated such a compound can then be formulated in an appropriate buffer and used as a therapeutic.

In addition, suitable therapeutics for the use of LCF or LCF agonists as immunosuppressive agents or as therapeutics to stimulate the expansion of CD4+ receptor bearing cells (as described supra) are formulated in an appropriate buffer such as physiological saline. Again, these formulations would be administered in a pharmaceutically-acceptable buffer (e.g., physiological saline).

Ordinarily, the therapeutic composition will be administered intravenously, at a dosage effective to stimulate activation of new CD4 lymphocyte populations; to induce anergy (see table above) and inhibit rejection in transplants; and to attenuate a hyperresponsive immune response and inflammation, e.g., asthma.

Alternatively, it may be convenient to administer the therapeutic orally, nasally, or topically, e.g. as a liquid or a spray as a primary product or as a viral vector carrying LCF cDNA. Again, the dosages are as described above. However, the dosage of the compound for treating any of the above-mentioned disorders varies depending upon the manner of administration, the age and the body weight of the subject, and the condition of the subject to be treated, and ultimately will be decided by the attending physician or veterinarian. Such amount of the active compound as determined by the attending physician or veterinarian is referred to herein as a "therapeutically effective amount." The compounds of the invention can be administered to a mammal, e.g., a human patient in a dosage of 0.5 μg/kg/day to 5 mg/kg/day.

Synergistic effect between recombinant LCF and growth factor (e.g., IL-2) are induced by sequential administration of recombinant LCF (0.5 μg/kg to 5 mg/kg followed in 24 hours by similar doses or rIL-2. As demonstrated above, rLCF and rIL-2 are effective in promoting the survival and proliferation of immune cells, e.g., HIV+PBMCs. Accordingly, compounds of the invention can be formulated according to known methods to prepare pharmaceutically useful compositions. Treatment of human patients will be carried out using in vivo and/or ex vivo administration of a therapeutically effective amount of rLCF and IL-2. Suitable carriers and their formulation are described for example in Remington's Pharmaceutical Sciences by E. W. Martin. The amount of the rLCF and IL-2 to be administered varies depending upon the manner of administration, the age and body weight of the patient, and with the type of disease, extensiveness of the disease, and size of the patient suffering from the disease. Generally amounts will be in the range of those used for other agents used in the treatment of other immune disease, e.g., AIDS. For example, for rLCF and rIL-2 is administered systemically, as at a dosage that promotes cell proliferation, typically in the range of 0.5 μg/kg/day to 5 mg/kg/day. Treatment is started generally with the diagnosis or suspicion of an immune disorder and is generally repeated on a daily basis. Protection from the development of an immune disorder, e.g., AIDS, is also achieved by administration of rLCF on a daily basis, and if desired, in combination with rIL-2. If desired, the efficacy of the treatment or protection regimens is assessed with standard methods of monitoring or diagnosing patients for an immune disorder. Reconstitution of the immune system, e.g., a patient's CD4+ cells, is useful in cellular immunotherapy for preventing, suppressing, or inhibiting the failure of the immune system, e.g. as found during HIV infection. In general, such treatment is useful for treating or delaying additional immunological and clinical deterioration.

The methods of the invention may be used to reduce the disorders described herein in any mammal, for example, humans, domestic pets, or livestock. Where a non-human mammal is treated, the LCF polypeptide or the antibody employed is preferably but not necessarily specific for that species.

OTHER EMBODIMENTS

The invention includes any protein which is substantially homologous to LCF polypeptide (FIG. 2, SEQ ID NO: 1). LCF is expressed in human T cells and exocrine pancreas. It is also expressed in the human monocytoid cell line THP-1. Also included are: allelic variations; natural mutants; induced mutants; proteins encoded by DNA that hybridizes under high or low (e.g., washing at 2×SSC at 40° C. with a probe length of at least 40 nucleotides) stringency conditions to a nucleic acid naturally occurring (for other definitions of high and low stringency see Current Protocols in Molecular Biology, John Wiley & Sons, New York, 1989); and polypeptides or proteins specifically bound by antisera to LCF polypeptide, especially by antisera to the active site or binding domain of LCF polypeptide. The term also includes chimeric polypeptides that include LCF polypeptide.

In addition to substantially full-length the invention also includes biologically active fragments of the polypeptides. As used herein, the term "fragment", as applied to a polypeptide, will ordinarily be at least about residues, more typically at least about 40 residues, preferably at least about 60 residues in length. Fragments of LCF polypeptide can be generated by methods known to those skilled in the art. The ability of a candidate fragment to exhibit a biological activity of LCF polypeptide can be assessed by methods known to those skilled in the art as described herein. Also included are LCF polypeptides containing residues that are not required for biological activity of the peptide such as residues that are not required for the biological activity of the polypeptide, or that result from alternative mRNA splicing or alternative protein processing events.

We claim:

1. A lymphocyte chemoattractant factor (LCF) immunoassay kit comprising an antibody which binds a LCF polypeptide having SEQ ID NO. 1.

2. The lymphocyte chemoattractant factor immunoassay kit of claim 1, further comprising means for detecting binding of said antibody to said lymphocyte chemoattractant factor polypeptide.

3. A method of detecting lymphocyte chemoattractant factor (LCF) in a biological sample, said method comprising:

(a) contacting said biological sample with an antibody which binds to lymphocyte chemoattractant factor having SEQ ID NO. 1; and (b) detecting immune complex formation, between said antibody and a sample constituent, as indicative of the presence of said lymphocyte chemoattractant factor in said sample.

4. The method of claim 3, wherein said immune complex formation is detected by ELISA.

5. The method of claim 3, wherein said immune complex formation is detected by Western blot analysis.

* * * * *

UNITED STATES PATENT AND TRADEMARK OFFICE
CERTIFICATE OF CORRECTION

PATENT NO.    : 5,766,866
DATED         : June 16, 1998
INVENTOR(S)   : David M. Center, et al.

It is certified that error appears in the above-identified patent and that said Letters Patent is hereby corrected as shown below:

Column 7,
Line 36: "(10g)" should read -- (10µg) --
Line 54: "a fold" should read -- a 100 fold --

Column 8,
Line 29: "fold" should read -- 100 fold --

Column 11,
Line 18: "α" should read -- 1β --

Column 12,
Line 50: "E. cole" should read -- E. coli --

Column 20,
Lines 25: "hr." should read -- 1 hr. --
Line 35: "hr." should read -- 1 hr --
Line 37: "10µl" should read -- 100µl --

Column 22,
Line 5: "below control" should read -- below chemotaxis control --

Column 30,
Line 59: "full–length the" should read -- full length polypeptides, the --

Signed and Sealed this

Eighteenth Day of September, 2001

*Attest:*

NICHOLAS P. GODICI
*Attesting Officer*     Acting Director of the United States Patent and Trademark Office